US008877229B2

(12) United States Patent
Campbell et al.

(10) Patent No.: US 8,877,229 B2
(45) Date of Patent: Nov. 4, 2014

(54) CONTROLLED RELEASE MICROPARTICLES

(75) Inventors: Kathleen M. Campbell, Longmont, CO (US); Pericles Calias, Melrose, MA (US); Gary P. Cook, Westford, MA (US); Mary A. Ganley, Norwood, MA (US)

(73) Assignee: Eyetech Inc., Palm Beach Gardens, FL (US)

( * ) Notice: Subject to any disclaimer, the term of this patent is extended or adjusted under 35 U.S.C. 154(b) by 1363 days.

(21) Appl. No.: 11/607,382

(22) Filed: Dec. 1, 2006

(65) Prior Publication Data
US 2007/0292475 A1    Dec. 20, 2007

Related U.S. Application Data

(60) Provisional application No. 60/741,741, filed on Dec. 2, 2005, provisional application No. 60/780,760, filed on Mar. 9, 2006, provisional application No. 60/796,071, filed on Apr. 28, 2006.

(51) Int. Cl.
| A61K 9/52 | (2006.01) |
| A61P 27/02 | (2006.01) |
| A61K 9/16 | (2006.01) |
| A61K 31/00 | (2006.01) |
| A61K 9/00 | (2006.01) |

(52) U.S. Cl.
CPC ............. *A61K 9/0048* (2013.01); *A61K 9/1647* (2013.01); *A61K 31/00* (2013.01)
USPC .......................................... 424/428; 424/489

(58) Field of Classification Search
None
See application file for complete search history.

(56) References Cited

U.S. PATENT DOCUMENTS

| 4,865,846 | A | * | 9/1989 | Kaufman ....................... 424/428 |
| 5,641,749 | A | * | 6/1997 | Yan et al. ........................ 514/12 |
| 6,506,399 | B2 | * | 1/2003 | Donovan ........................ 424/423 |
| 2003/0211164 | A1 | * | 11/2003 | Wright et al. .................. 424/490 |
| 2005/0244467 | A1 | * | 11/2005 | Nivaggioli et al. ............ 424/427 |

FOREIGN PATENT DOCUMENTS

| WO | WO-03092665 A2 | 11/2003 |
| WO | WO 2004/073551 | * 9/2004 |
| WO | WO-2005110473 A2 | 11/2005 |
| WO | WO-2005110489 A2 | 11/2005 |

OTHER PUBLICATIONS

Carrasquillo et al., "Non-aqueous encapsulation of excipient-stabilized spray-freeze dried BSA into poly(lactide-co-glycolide) microspheres results in release of native protein", J. Control Release, 2001, 76:199-208.*

(Continued)

*Primary Examiner* — Ernst V Arnold
*Assistant Examiner* — Jianfeng Song
(74) *Attorney, Agent, or Firm* — Mintz Levin Cohn Ferris Glovsky and Popeo, P.C.; Fred C. Hernandez; Shovon Ashraf

(57) ABSTRACT

Formulations for controlled, sustained release of biologically active agents for the treatment of ocular disorders have been developed. These formulations are based on solid microparticles formed of the combination of biodegradable, synthetic polymers such as poly(lactic acid) (PLA), poly(glycolic acid) (PGA), and copolymers thereof. The microparticles are characterized by low burst levels and efficient drug loading and sustained release.

39 Claims, 17 Drawing Sheets

(56) References Cited

OTHER PUBLICATIONS

Carrasquillo et al. "Controlled Delivery of the Anti-VEGF Aptamer EYE001 with Poly(lactic-*co*-glycolic) Acid Microspheres." *Invest. Ophthalmol. Vis. Sci.* 44.1(2003):290-299.

Drolet et al. "Pharmacokinetics and Safety of an Anti-Vascular Endothelial Growth Factor Aptamer (NX1838) Following Injection into the Vitreous Humor of Rhesus Monkeys." *Pharma Res.* 17.12(2000):1503-1510.

The Eyetech Study Group. "Anti-Vascular Endothelial Growth Factor Therapy for Subfoveal Choroidal Neovascularization Secondary to Age-Related Macular Degeneration." *Ophthalmol.* 110.5(2003):979-986.

The Eyetech Study Group. "Preclinical and Phase 1A Clinical Evaluation of an Anti-VEGF Pegylated Aptamer (EYE001) for the Treatment of Exudative Age-Related Macular Degeneration." *Retina.* 22.2(2002):143-152.

* cited by examiner

CONTROLLED RELEASE MICROPARTICLES

RELATED APPLICATIONS

This application claims priority to U.S. Provisional Application Ser. No. 60/741,741, filed Dec. 2, 2005, and U.S. Provisional Application Ser. No. 60/780,760, filed Mar. 9, 2006, and U.S. Provisional Application Ser. No. 60/796,071, filed Apr. 28, 2006, all of which are hereby incorporated in its entirety by reference.

FIELD OF THE INVENTION

The invention relates to drug delivery. In particular, the invention relates to compositions and methods for the sustained delivery of therapeutic agents using microparticles. More particularly, the invention relates to sustained release microparticle compositions and methods of use for ophthalmic administration.

BACKGROUND OF THE INVENTION

As new treatment modalities for ophthalmic diseases become available, the number of intravitreous injections administered is expected to increase dramatically. For example, intravitreous injection of the vascular endothelial growth factor (VEGF) inhibitor, Macugen® ((OSI) Eyetech, Inc. NY, N.Y.), has become available for the treatment of age-related macular degeneration. Macugen is currently delivered via intravitreous injection every six weeks.

Advantages of intravitreous injection of medicines and diagnostics include the achievement of maximum vitreous concentrations while minimizing toxicity attributed to systemic administration. While these advantages are becoming widely appreciated, the ophthalmology community turns its focus to various complications potentially associated with intravitreous injection. Risks of intravitreous injection, some vision threatening, include endophthalmitis, retinal detachment, iritis/uveitis, inflammation, intraocular hemorrhage, ocular hypertension, hypotony, pneumatic retinopexy, and cataract (R. D. Jager et al., *Retina* 24:676-698, 2004 and C. N. Ta, *Retina*, 24:699-705, 2004). Methods of minimizing such risks include developing sustained release ophthalmic formulations to minimize the number of intraocular injections.

Ophthalmic inserts are solid devices intended to be placed in the conjunctival sac and to deliver the drug at a comparatively slow rate. One such device is Ocusert® (Alza Corporation, Mountain View, Calif.), which is a diffusion unit consisting of a drug reservoir enclosed by two release-controlling membranes made of a copolymer. M. F. Saettone provides a review of continued endeavors devoted to ocular delivery. ("Progress and Problems in Ophthalmic Drug Delivery", *Business Briefing: Pharmatech, Future Drug Delivery*, 2002, 167-171). Other implant strategies have been developed for small, highly potent, lipophilic therapeutics. (G. A. Peyman, et al., "Delivery Systems for Intraocular Routes" *Advanced Drug Delivery Reviews*, (1995) 16, 107.) While these implants are effective for the delivery of steroids, the small size of the implants preclude long-term (>30 days) delivery of large, water-soluble compounds. In addition, formulation conditions for most polymeric delivery systems are not compatible with proteins, antibodies, and other biotherapeutics (S. P. Schwendeman et al., "Peptide, protein, and vaccine delivery from implantable polymeric systems: Progress and challenges" *Controlled Drug Delivery*, (1997) 229).

Encapsulation of pharmaceuticals in biocompatible, biodegradable polymer microparticles can prolong the maintenance of therapeutic drug levels relative to administration of the drug itself. Sustained release may be extended up to several months depending on the formulation and the active molecule encapsulated. In order to prolong the existence at the target site, the drug may be formulated within a matrix into a slow release formulation (see, for example, Langer (1998) *Nature*, 392, Supplement, 5-10). Following administration, drug then is released via diffusion out of, or via erosion of the matrix. Encapsulation within biocompatible, biodegradable polyesters, for example, copolymers of lactide and glycolide, has been utilized to deliver small molecule therapeutics ranging from insoluble steroids to small peptides. Presently, there are over a dozen lactide/glycolide polymer formulations in the marketplace, the majority of which are in the form of microparticles (T. Tice, "Delivery with Depot Formulations" *Drug Delivery Technology*, (2004) 4(1)).

Several techniques for the production of lactide/glycolide polymer microparticles containing biological or chemical agents by an emulsion-based manufacturing technique have been reported. In general, the methods include preparation of a first phase consisting of an organic solvent, a polymer and a biological or chemical agent dissolved or dispersed in the first solvent. A second phase comprises water and a stabilizer and, optionally, the first solvent. The first and second phases are emulsified and, after an emulsion is formed, the first solvent is removed from the emulsion, producing hardened microparticles.

Microparticles can also be produced using a water-in-oil-in-water (w/o/w) process. W/o/w emulsions can be considered as an aqueous emulsion of oil droplets which in turn contain a dispersed aqueous phase. Examples of w/o/w emulsion processes are described in U.S. Pat. Nos. 4,954,298; 5,330,767; 5,851,451 and 5,902,834, each of which are hereby incorporated herein by reference in their entirety. The w/o/w process described above is typically used for water-soluble molecules.

In addition, U.S. Pat. No. 6,706,289, hereby incorporated in its entirety by reference, discloses controlled release formulations of biologically active molecules that are coupled to hydrophilic polymers such as polyethylene glycol and methods of their production. The formulations are based on solid microparticles formed of the combination of biodegradable, synthetic polymers such as poly(lactic acid) (PLA), poly (glycolic acid) (PGA), and copolymers thereof. PCT WO 03/092665, hereby incorporated in its entirety by reference, discloses microsphere formulations for the sustained delivery of an aptamer, for example, an anti-Vascular Endothelial Growth Factor aptamer, to a pre-selected locus in a mammal. Such formulations are further disclosed in K. G. Carrasquillo et al., "Controlled Delivery of the Anti-VEGF Aptamer EYE001 with Poly(lactic-co-glycolic) Acid Microspheres," *I.O.V.S.* (2003) 44(1), 290.

Patient acceptance and safety are key issues that will play a role in which treatments are used. Frequent intraocular injections may not be favorable because they cause patient discomfort and sometimes fear, while risking permanent tissue damage. Therefore there remains a need for developing sustained release ophthalmic formulations to minimize the number of intraocular injections.

SUMMARY OF THE INVENTION

The present invention provides compositions and methods for the sustained delivery of a biologically active agent using microparticles. In a particular aspect, the present invention provides sustained release microparticle compositions and methods for ophthalmic administration.

In one aspect, the present invention provides a composition comprising sustained release microparticles having the ability to be administered by syringe to the eye. According to this aspect, the present invention provides microparticle formulations syringable through a 27-gauge needle or narrower (smaller).

In one embodiment, the microparticles release a biologically active agent over a period of at least about 1-12 months. In a further embodiment, the microparticles release a biologically active agent over a period of at least about 3-6 months.

In another embodiment, the microparticles have a core load of at least about 10% by weight of the biologically active agent.

In another embodiment, the microparticles have an initial 24-hour in vivo burst of less than about 10% by weight of the core load of the biologically active agent.

In another aspect, the present invention provides compositions and methods for the sustained delivery of an aptamer conjugated to a hydrophilic polymer such as polyethylene glycol. According to a particular embodiment, the aptamer comprises pegaptanib.

In another aspect, the present invention provides compositions and methods for the sustained delivery of an anti-VEGF agent. According to a particular embodiment, the anti-VEGF agent comprises an aptamer.

In another aspect, the present invention provides a composition comprising sustained release microparticles comprising pegaptanib having the ability to be administered to a subject by a syringe via a 27-gauge needle or smaller.

In one embodiment, the microparticles release pegaptanib over a period of at least about 1-12 months. In another embodiment, the microparticles release pegaptanib over a period of at least about 3-6 months.

In another embodiment, the microparticles have a core load of at least about 10% by weight of pegaptanib.

In another embodiment, the microparticles have an initial 24-hour in vivo burst of less than about 10% by weight of the core load of pegaptanib.

In another aspect, the present invention provides methods of administering sustained release microsphere formulations to achieve a desired pharmacokinetic profile. According to one embodiment, microparticles comprising a biologically active agent are suspended in a pharmaceutically acceptable solution and administered by syringe to the eye.

According to another embodiment, microparticles comprising a biologically active agent are suspended in a solution comprising the biologically active agent and administered by syringe to the eye. Utilizing the vitreal residence time of the biologically active agent as a polymer clearance window allows the polymeric metabolites to be cleared while sustaining a therapeutically relevant level within the eye.

The present invention has several advantages. In particular, the microparticles of the present invention are easily suspendable and syringable while able to provide increased duration, increased stability, decreased burst and controlled, sustained or delayed release of biologically active molecules in vivo.

DETAILED DESCRIPTION OF THE INVENTION

The present invention provides compositions and methods for the sustained delivery of a biologically active agent. In one aspect, the present invention provides compositions and methods for ocular sustained delivery of a biologically active agent. According to this aspect, syringable microsphere formulations are provided for administering a biologically active agent with a syringe via a 27-gauge needle or smaller in order to provide sustained ocular levels of the biologically active agent.

Figure 1:
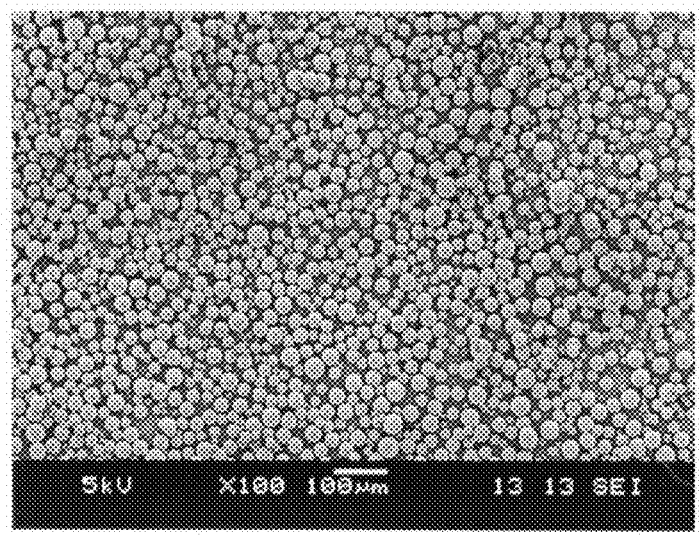
FIG. 1 is a scanning electron micrograph showing the external morphology of a sample of microspheres of the present invention.
Figure 1:
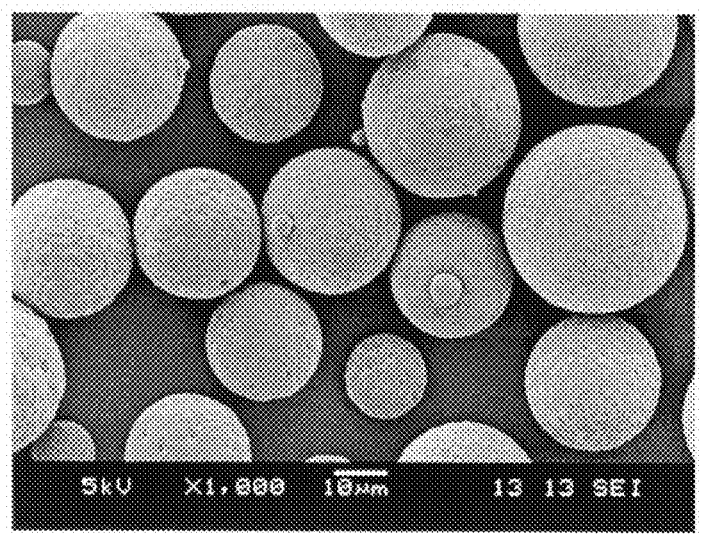
Figure 2:
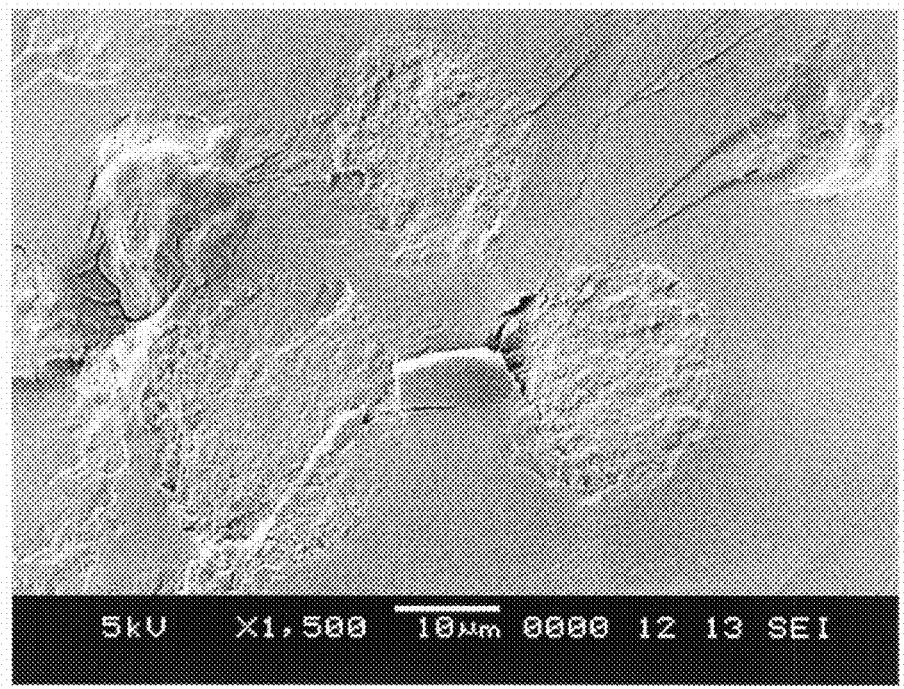
FIG. 2 is a scanning electron micrograph of cross-sectioned pegaptanib-PLGA microspheres of the present invention having a low burst release.

Microparticles can vary in size, ranging from submicron to millimeter diameters. For ophthalmic applications, the diameters of the microparticles range from about 1 micron (μm) to about 200 μm. In another embodiment, the microparticles have a particle size distribution ranging from about 1 μm to about 100 μm in diameter. In another embodiment, the microparticles have a particle size distribution ranging from about 10 μm to about 50 μm in diameter.

In another embodiment, the microparticles have an average diameter of less than about 45 μm. In another embodiment, the microparticles have an average diameter of about 30 μm. In another embodiment, the microparticles have an average diameter of about 15 μm.

In one embodiment, the microparticles are of a suitable size and morphology allowing for delivery though a needle having a small inner-diameter such as a narrow (small) gauge needle. In a particular embodiment, the microparticles are of a suitable size and morphology allowing for delivery though a needle suitable for ophthalmic administration. Microparticles are referred to herein as "syringable" if the are able to be delivered though a needle. In one embodiment, the microparticles are syringable through a medically acceptable needle. In another embodiment, the microparticles are syringable through a needle suitable for ophthalmic administration. Example 7 provides methods for analyzing suspendability and syringability.

In one particular embodiment particularly suited for ophthalmic applications, the microparticles are syringable through a needle having a gauge of at least 27 having a nominal inner diameter of 0.0075 inches or less. In another particular embodiment the microparticles are syringable through a needle having a gauge of at least 29 having a nominal inner diameter of 0.0065 inches or less. In another particular embodiment the microparticles are syringable through a needle having a gauge of at least 30 having a nominal inner diameter of 0.0055 inches or less.

In one embodiment, the microparticles have a mean diameter of less than or equal to about 75% of the inner diameter of the needle used for injection. In another embodiment, the microparticles have a mean diameter of less than or equal to about 50% of the inner diameter of the needle used for injection. In another embodiment, the microparticles have a mean diameter of less than or equal to about 25% of the inner diameter of the needle used for injection. In another embodiment, the microparticles have a mean diameter of less than or equal to about 10% of the inner diameter of the needle used for injection.

In one embodiment, the microparticles form free-flowing and/or un-agglomerated powders. Free-flowing and/or un-agglomerated powders are advantageous because they roll with substantially no friction and can be easily placed in containers, suspended or incorporated into a solution suitable for injection. Flowabilty of microparticles can be measured by any suitable means such as a Jenike Shear Tester (Jenike & Johanson, Inc., Westford, Mass.), which measures the direct shear strength of powders and other bulk solid materials. Using a Jenike Shear Tester, a shear cell (base and ring) is filled with material; a vertical load is applied to the covered cell, using weights and the weight carrier; and the shear cell ring is pushed horizontally across the base, with the required force measured and recorded. Other apparatuses for measuring flowability include a powder rheometer (Freeman Technology, Worcestershire, UK) that measures the force of a twisted blade along a helical path through a powder sample establishing a required flow rate and pattern of flow. A critical orifice and an angle of repose using an avalanche process may also be measured.

A chart representing particle size distribution of typical microparticles before sieving is shown in FIG. 7.

The microparticles of the present invention have a core load sufficient to deliver the biologically active agent to maintain therapeutically effective levels of the biologically active agent for sustained periods. In one embodiment, the microparticles have a core load of greater than or equal to about 5% by weight of the biologically active agent. In one embodiment, the microparticles have a core load of greater than or equal to about 10% by weight of the biologically active agent. In one embodiment, the microparticles have a core load of greater than or equal to about 15% by weight of the biologically active agent. In another embodiment the microparticles have a core load of greater than or equal to about 20% by weight of the biologically active agent. In another embodiment the microparticles have a core load of greater than or equal to about 30% by weight of the biologically active agent.

In one embodiment, microparticles comprising pegaptanib have a core load of greater than or equal to about 10% by weight of pegaptanib (2% by weight on an aptamer basis). In one embodiment, the microparticles have a core load of greater than or equal to about 15% by weight of pegaptanib (about 3% by weight on an aptamer basis).

The microparticles of the present invention exhibit a low initial burst. In one embodiment, the microparticles exhibit an initial 24 hour in vitro burst of less than or equal to about 10 wt % of the initial core load of the biologically active agent. In one embodiment, the microparticles exhibit an initial 24 hour in vitro burst of less than or equal to about 5 wt % of the initial core load of the biologically active agent.

The microparticles of the present invention provide a sustained release of a biologically active agent. In one embodiment the microparticles have an in vivo sustained release profile of at least 28 days (4 weeks/1 month). In another embodiment the microparticles have an in vivo sustained release profile of at least about 20, 40, 60 (2 months), 90 (3 months), 180 days (6 months), or 365 days (12 months).

In one embodiment the microparticles encapsulate pegaptanib as the biologically active agent and are adapted to release pegaptanib at a rate ranging from about 0.01 to about 10 micrograms (μg) per day. In another embodiment, the microparticles encapsulate pegaptanib as the biologically active agent and are adapted to release pegaptanib at a rate ranging from about 0.1 to about 6 μg per day. In one particular embodiment pegaptanib microparticles release pegaptanib at a rate of about 0.025 μg, 0.25 μg, 0.5 μg, 0.75 μg, 1 μg, or 2 μg per day.

The microparticles of the present invention have a high encapsulation efficiency. In one embodiment, the microparticles have an encapsulation efficiency of greater than or equal to about 80%. In another embodiment the microparticles have an encapsulation efficiency of greater than or equal to about 90%. In another embodiment the microparticles have an encapsulation efficiency of greater than or equal to about 95%. In another embodiment the microparticles have an encapsulation efficiency of about 100%.

The microparticles of the present invention have any suitable morphology. In one embodiment, the microparticles are solid. In another embodiment, the microparticles are smooth or non-pitted. In another embodiment, the microparticles are homogenous or monolithic. In another embodiment, the microparticles have a morphology allowing for a high core load, high encapsulation efficiency, low burst, sustained release and syringability.

FIGS. 1 and 2 show images of examples of microparticles of the present invention. External morphological examination of the microparticles in FIG. 1 indicates that the microparticles are smooth and non-pitted. Internal morphological examination of the microparticles in FIG. 2 indicates microparticles have a monolithic interior. Monolithic microparticles give consistent release kinetics.

Example 7 describes an experimental for the analysis of in vitro release of microparticle formulations of the present invention formed by the process as described in Examples 1 and 2. The results of the in vitro release analysis are depicted in FIGS. 9, 10, 13, and 16. The results shown in the figures demonstrate the sustained release properties of the microparticles of the present invention. The results shown in the figures also demonstrate that the microparticles of the present invention can be selectively designed to control the release of a biologically active agent over a desired time period.

In another aspect, the present invention provides methods of administering sustained release microparticle formulations to achieve a desired pharmacokinetic profile. According to one embodiment, microparticles comprising a biologically active agent are suspended in a pharmaceutically acceptable solution and administered by syringe to the eye.

In another aspect, the present invention provides controlled release of a biologically active agent in accordance with a desired pharmacokinetic profile. The microparticles of the present invention may be suspended in a solution containing an additional amount of the same biologically active agent or a second biologically active agent. This solution containing the dissolved biologically active agent may provide a desired bolus of the agent to achieve a therapeutically effective level, which is subsequently maintained for a prolonged period by the sustained release microparticles.

According to one embodiment, microparticles comprising a biologically active agent are suspended in a solution comprising the biologically active agent and administered by syringe to the eye. In one embodiment, the microparticles are sustained release microparticles. In another embodiment, the microparticles are delayed release microparticles. Utilizing the vitreal residence time of the biologically active agent as a polymer clearance window allows the polymeric metabolites to be cleared while sustaining a therapeutically relevant level within the eye. Utilizing the vitreal residence time of the biologically active agent as a polymer clearance window also allows a staggered multiple bolus of a biologically active agent using a single administration. Such a dosing regimen may be particularly useful for microencapsulated biologically active agents that have some residence time in the vitreous.

Examples of ocular formulations comprising a suspension of a particle including an ophthalmic drug and a liquid carrier containing at least the same ophthalmic drug is described in U.S. Pat. Nos. 4,882,150 and 4,865,846, the contents of each are incorporated herein by reference in their entirety.

In one embodiment, the regimen comprises the step of administering a pharmaceutical formulation comprising a first bolus of a first biologically active agent and a delayed release microparticle formulation encapsulating a second bolus of the first biologically active agent.

In a particular embodiment, the regimen comprises the step of administering about 100 µL of a pharmaceutical formulation comprising a bolus of about 0.3 mg free pegaptanib in solution and delayed release PLGA microparticles encapsulating about 35 mg pegaptanib. The microparticles have an initial burst of about 5-30% of pegaptanib and then will release at a constant rate over about a 1-month time period. At the end of the microparticle release profile, a second burst will occur releasing a second bolus of pegaptanib bringing the vitreal concentration to about 0.3 mg. In another particular embodiment the regimen further comprises the step of administering a second pharmaceutical formulation comprising pegaptanib at a time of four weeks post after the second burst, during which time the polymeric metabolites are cleared. In this embodiment, the administration essentially gains an additional month of efficacy.

One advantage of such a regimen includes the reduction of multiple intravitreous injections of polymer encapsulated biologically active agents. Another advantage includes limiting any possible risk of having the clearance pathways of the eye hindered by a buildup of polymeric breakdown products causing detrimental effects on ocular function.

The microparticles of the present invention can be used for any purpose. In a particular embodiment, they are administered to a patient. They may be administered to patients in a single or multiple dose. The microparticles may also be administered in a single dose form that functions to release a biologically active agent over a prolonged period of time, eliminating the need for multiple administrations.

In one aspect, the invention provides a method of treating or inhibiting an ocular disease state in a mammal in need thereof using any of the microsphere compositions described herein. The method includes administering the microparticles to a mammal in amounts sufficient to treat or inhibit the disease. In one embodiment, in order to treat an ocular disorder, the microparticles are injected into the vitreous of the eye (intravitreous injection). In another embodiment, in order to treat an ocular disorder, the microparticles are disposed upon the outer surface of the sclera (sub-conjunctival injection). In such a system, once the biologically active agent is released out of the microparticle, the biologically active agent traverses the sclera to exert its effect, for example, reduce or inhibit the activity of a VEGF receptor, within the eye.

The microparticles may be used to treat a variety of ocular disorders including, for example, optic disc neovascularization, iris neovascularization, retinal neovascularization, choroidal neovascularization, corneal neovascularization, vitreal neovascularization, glaucoma, pannus, pterygium, macular edema, vascular retinopathy, retinal degeneration, uveitis, inflammatory diseases of the retina, and proliferative vitreoretinopathy. The corneal neovascularization to be treated or inhibited may be caused by trauma, chemical burns and corneal transplantation. The iris neovascularization to be treated or inhibited may be associated with diabetic retinopathy, vein occlusion, ocular tumor and retinal detachment. The retinal neovascularization to be treated or inhibited may be associated with diabetic retinopathy, vein occlusion, sickle cell retinopathy, retinopathy of prematurity, retinal detachment, ocular ischemia and trauma. The intravitreous neovascularization to be treated or inhibited may be associated with diabetic retinopathy, vein occlusion, sickle cell retinopathy, retinopathy of prematurity, retinal s detachment, ocular ischemia and trauma. The choroidal neovascularization to be treated or: inhibited may be associated with retinal or subretinal disorders, such as, age-related macular degeneration, presumed ocular histoplasmosis syndrome, myopic degeneration, angioid streaks and ocular trauma.

Ophthalmic solutions are sterile solutions, essentially free from foreign particles, suitably compounded and packaged for instillation or injection into the eye. Preparation of an ophthalmic solution requires careful consideration of such factors as the inherent toxicity of the drug itself, isotonicity value, the need for buffering agents, the need for a preservative (and, if needed, its selection), sterilization, and proper packaging.

While specific reference has been made to the use of the formulations of the present invention to administer biologically active agent to the eye, it is to be understood that the present invention can be used to deliver a biologically active agent to any desired site, including, but not limited to, intraorbital, intraocular, intraaural, intratympanic, intrathecal, intracavitary, peritumoral, intratumoral, intraspinal, epidural, intracranial, and intracardial. While referring to the eye, the formulations of the present invention may be administered intravitreously or periocularly (retrobulbarly, sub-tenonly, sub-conjunctivaly).

According to one embodiment, the microsphere formulations of the present invention are suitable for local application for the treatment of various cancers. According to this embodiment, the microsphere formulations are injected locally at the tumor site or post-operatively at the tumor site after tumor resection. According to this embodiment, microsphere formulations and related methods of use are provided for treating various difficult to treat cancers such as glioblastoma multiforme, ovarian cancer, and head or neck cancer, for example.

A formulation of the invention may be used in the treatment of any eye disease. A formulation of the invention may also be used to direct a biologically active agent to a particular eye tissue, e.g., the retina or the choroid. The biologically active agent or combination of agents will be chosen based on the disease, disorder, or condition being treated. In addition to a biologically active agent for a particular condition, other compounds may be included for secondary effects, for example, an antibiotic to prevent microbial growth. The amount and frequency of the dosage will depend on the disease, disorder, or condition being treated and the biologically active agent employed. One skilled in the art can make this determination.

By "treating" is meant the medical management of a patient with the intent that a cure, amelioration, stasis or prevention of a disease, pathological condition, or disorder will result. This term includes active treatment, that is, treatment directed specifically toward improvement of a disease, pathological condition, or disorder, and also includes causal treatment, that is, treatment directed toward removal of the cause of the disease, pathological condition, or disorder. In addition, this term includes palliative treatment, that is, treatment designed for the relief of symptoms rather than the curing of the disease, pathological condition, or disorder; preventive treatment, that is, treatment directed to prevention of the disease, pathological condition, or disorder; and supportive treatment, that is, treatment employed to supplement another specific therapy directed toward the improvement of the disease, pathological condition, or disorder. The term "treating" also includes symptomatic treatment, that is, treatment directed toward constitutional symptoms of the disease, pathological condition, or disorder.

In one embodiment, the method of the invention provides a means for suppressing or treating an ocular neovascular disorder. In some embodiments, ocular neovascular disorders amenable to treatment or suppression by the method of the invention include ischemic retinopathy, iris neovascularization, intraocular neovascularization, age-related macular degeneration, corneal neovascularization, retinal neovascularization, choroidal neovascularization, retinopathy of prematurity, retinal vein occlusion, diabetic retinal ischemia, diabetic macular edema, or proliferative diabetic retinopathy. In still another embodiment, the method of the invention provides a means for suppressing or treating psoriasis or rheumatoid arthritis in a patient in need thereof or a patient diagnosed with or at risk for developing such a disorder.

As used herein, the terms "neovascularization" and "angiogenesis" are used interchangeably. Neovascularization and angiogenesis refer to the generation of new blood vessels into cells, tissue, or organs. The control of angiogenesis is typically altered in certain disease states and, in many cases, the pathological damage associated with the disease is related to altered, unregulated, or uncontrolled angiogenesis. Persistent, unregulated angiogenesis occurs in a multiplicity of disease states, including those characterized by the abnormal growth by endothelial cells, and supports the pathological damage seen in these conditions including leakage and permeability of blood vessels.

By "ocular neovascular disorder" is meant a disorder characterized by altered or unregulated angiogenesis in the eye of a patient. Exemplary ocular neovascular disorders include optic disc neovascularization, iris neovascularization, retinal neovascularization, choroidal neovascularization, corneal neovascularization, vitreal neovascularization, glaucoma, pannus, pterygium, macular edema, diabetic retinopathy, diabetic macular edema, vascular retinopathy, retinal degeneration, uveitis, inflammatory diseases of the retina, and proliferative vitreoretinopathy.

In addition to treating pre-existing neovascular disorders, the therapy that includes a biologically active agent can be administered prophylactically in order to prevent or slow the onset of these disorders. In prophylactic applications, the biologically active agent is administered to a patient susceptible to or otherwise at risk of a particular neovascular disorder. The precise timing of the administration and amounts that are administered depend on various factors such as the patient's state of health, weight, etc.

A "biologically active agent", "biologically active moiety" or "biologically active molecule" can be any substance which can affect any physical or biochemical properties of a biological organism, including but not limited to, viruses, bacteria, fungi, plants, animals, and humans. Biologically active molecules can include any substance intended for diagnosis, cure mitigation, treatment, or prevention of disease in humans or other animals, or to otherwise enhance physical or mental well-being of humans or animals.

Examples of biologically active agents include, but are not limited to, nucleic acids, nucleosides, oligonucleotides, antisense oligonucleotides, RNA, DNA, siRNA, RNAi, aptamers, antibodies, peptides, proteins, enzymes, fusion proteins, porphyrins, and small molecule drugs. Other biologically active agents include, but are not limited to, dyes, lipids, cells, viruses, liposomes, microparticles and micelles. Examples of antibodies include, but are not limited to, anti-VEGF antibodies bevacizumab (Avastin™) and ranizumab (Lucentis™). Examples of aptamers include, but are not limited to, pegaptanib (Macugen®). Examples of porphyrins include, but are not limited to, verteporfin (Visudine®). Examples of steroids include, but are not limited to, anecortave acetate (Retaane®). Examples of fusion proteins include, but are not limited to, VEGF Trap™ (Regeneron Pharmaceuticals, Inc. Tarrytown, N.Y.). Examples of RNAi include, but are not limited to, Direct RNAi™ (Alnylam Pharmaceuticals, Cambridge, Mass.).

Classes of biologically active agents that are suitable for use with the invention include, but are not limited to, antibiotics, fungicides, anti-viral agents, anti-infective agents, anti-inflammatory agents, anti-tumor agents, anti-tubulin agents, cardiovascular agents, anti-anxiety agents, hormones, growth factors, steroidal agents, and the like.

The term "anti-VEGF agent" refers to any biologically active agent where the primary mode of action is to (a) impair binding of any VEGF isoform to its receptor, or (b) block signaling of VEGF receptors R1 and R2.

It will be understood that pharmaceutically acceptable salts of the biologically active molecule disclosed herein are also included in the present invention and can be used in the compositions and methods disclosed herein.

The term "oligonucleotide" refers to an oligomer or polymer of nucleotide or nucleoside monomers consisting of naturally occurring bases, sugars and inter-sugar (backbone) linkages. The term also includes modified or substituted oligomers comprising non-naturally occurring monomers or portions thereof, which function similarly. Incorporation of substituted oligomers is based on factors including enhanced cellular uptake, or increased nuclease resistance and are chosen as is known in the art. The entire oligonucleotide or only portions thereof may contain the substituted oligomers.

As used herein, the term "aptamer" means any polynucleotide, or salt thereof, having selective binding affinity for a non-polynucleotide molecule via non-covalent physical interactions. An aptamer can be a polynucleotide that binds to a ligand in a manner analogous to the binding of an antibody to its epitope. The target molecule can be any molecule of interest. An example of a non-polynucleotide molecule is a protein. An aptamer can be used to bind to a ligand-binding domain of a protein, thereby preventing interaction of the naturally occurring ligand with the protein.

"Anti-VEGF aptamers" or "VEGF aptamers" are meant to encompass polynucleotide aptamers that bind to, and inhibit the activity of, VEGF. Such anti-VEGF aptamers may be RNA aptamers, DNA aptamers or aptamers having a mixed (i.e., both RNA and DNA) composition. Such aptamers can be identified using known methods. For example, Systematic Evolution of Ligands by Exponential enrichment, or SELEX, methods can be used as described in U.S. Pat. Nos. 5,475,096 and 5,270,163, each of which are incorporated herein by reference in its entirety. Anti-VEGF aptamers include the sequences described in U.S. Pat. Nos. 6,168,778, 6,051,698, 5,859,228, and 6,426,335, each of which are incorporated herein by reference in its entirety. The sequences can be modified to include 5'-5' and/or 3'-3' inverted caps. (See Adamis, A. P. et al., published application No. WO 2005/014814, which is hereby incorporated by reference in its entirety).

For ophthalmic drug delivery applications, exemplary disease states include macular degeneration (dry and wet), diabetic retinopathy, glaucoma, optic disc neovascularization, iris neovascularization, retinal neovascularization, choroidal neovascularization, pannus, pterygium, macular edema, vascular retinopathy, retinal vein occlusion, histoplasmosis, ischemic retinal disease, retinal degeneration, uveitis, inflammatory diseases of the retina, keratitis, cytomegalovirus retinitis, an infection, conjunctivitis, cystoid macular edema, cancer, and proliferative vitreoretinopathy.

Classes of biologically active agents include anti-infectives including, without limitation, antibiotics, antivirals, and antifungals; analgesics; antiallergenic agents; mast cell stabilizers; steroidal and non-steroidal anti-inflammatory agents; decongestants; anti-glaucoma agents including, without limitation, adrenergics, beta-adrenergic blocking agents, alpha-adrenergic blocking agonists, parasympathomimetic agents, cholinesterase inhibitors, carbonic anhydrase inhibitors, and protaglandins; antioxidants; nutritional supplements; angiogenesis inhibitors; antimetabolites; fibrinolytics; wound modulating agents; neuroprotective drugs; angiostatic steroids; mydriatics; cyclopegic mydriatics; miotics; vasoconstrictors; vasodilators; anticlotting agents; anti-cancer agents; immunomodulatory agents; VEGF antagonists; immunosuppresant agents; and combinations and prodrugs thereof.

The biologically active agent may be conjugated to non-toxic long-chain polymers such as poly(ethylene glycol) (PEG). Such polymers may increase blood circulation lifetimes, improve efficacy and safety, and increase stability. Competitive binding studies of aptamers utilizing this strategy revealed that the PEG unit actively assists in the inhibitory potency of Macugen, specifically with its ability to prevent VEGF binding to the Flt-1 receptor. (US Patent Application Publication No. US 2005/0260651, which is hereby incorporated herein by reference in its entirety) While the clinical relevance is uncertain, strong evidence indicates that inhibition of Flt-1 binding is a major contributor to the anti-inflammatory properties of Macugen (Usui, T. et al. (2004) "VEGF164(165) as the Pathological Isoform: Differential Leukocyte and Endothelial Responses through VEGFR1 and VEGFR2." *I.O.V.S.* 45(2), 368).

Specific biologically active agents include MACUGEN® (pegaptanib sodium injection) as described in U.S. Pat. No. 6,051,698, herein incorporated in its entirety by reference. Pegaptanib is also referred to as EYE001 (previously referred to as NX1838).

Pegaptanib is a covalent conjugate of an oligonucleotide of twenty-eight nucleotides in length that terminates in a pentylamino linker, to which two 20-kilodalton (kDa) monomethoxypolyethylene glycol (PEG) units are covalently attached via the two amino groups on a lysine residue. Pegaptanib is optionally provided in the form of a pharmaceutically acceptable salt. In one embodiment, pegaptanib is provided as pegaptanib sodium. The molecular formula for pegaptanib sodium is $C_{294}H_{342}F_{13}N_{107}Na_{28}O_{188}P_{28}(C_2H_4O)_n$ (where n is approximately 900) and the molecular weight is approximately 50 kDa.

The chemical name for pegaptanib sodium is as follows: RNA, ((2'-deoxy-2'-fluoro)C-$G_m$-$G_m$-AA-(2'-deoxy-2'-fluoro)U-(2'-deoxy-2'-fluoro)C-$A_m$-$G_m$-(2'-deoxy-2'-fluoro)U-$G_m$-$A_m$-$A_m$-(2'-deoxy-2'-fluoro)U-$G_m$-(2'-deoxy-2'-fluoro)C-(2'-deoxy-2'-fluoro)U-(2'-deoxy-2'-fluoro)U-$A_m$-(2'-deoxy-2'-fluoro)U-$A_m$-(2'-deoxy-2'-fluoro)C-$A_m$-(2'-deoxy-2'-fluoro)U-(2'-deoxy-2'-fluoro)C-(2'-deoxy-2'-fluoro)C-$G_m$-(3'→3')-dT), 5'-ester with α,α'-[4,12-dioxo-6-[[[5-(phosphoonoxy)pentyl]amino]carbonyl]-3,13-dioxa-5,11-diaza-1,15-pentadecanediyl]bis[(ω-methoxypoly(oxy-1,2-ethanediyl)], sodium salt.

Dosage levels of pegaptanib sodium on the order of about 1 μg/kg to 100 mg/kg of body weight per administration are useful in the treatment of neovascular disorders. Examples of formulations are found in WO 03/039404, which is hereby incorporated by reference in its entirety. In some embodiments, pegaptanib sodium is administered at a dosage of about 0.1 mg to about 1.0 mg locally into the eye, wherein the treatment is effective to treat occult, minimally classic, and predominantly classic forms of wet macular degeneration. When administered directly to the eye, the dosage range is about 0.3 mg to about 3 mg per eye, in some embodiments the dosage range is about 0.1 mg to about 1.0 mg per eye. In one embodiment, pegaptanib sodium is administered in a therapeutically effective amount of about 0.1-3.0 mg, 0.1-1.0 mg, or about 0.3 mg. In one embodiment, pegaptanib sodium is present in an ophthalmic injection solution formulation at a concentration ranging from 0.1 to 3.0 mg/mL. According to one embodiment, the carrier comprises sodium phosphate and sodium chloride. According to one specific embodiment the carrier comprises 10 mM sodium phosphate and 0.9% sodium chloride.

According to one embodiment, the dose is effective to achieve a vitreous concentration of the anti-VEGF aptamer of about 10-30 ng/mL. According to another embodiment, the dose is effective to maintain a vitreous concentration of the anti-VEGF aptamer of about 10-30 ng/mL throughout the administration period.

In alternative embodiments, the anti-VEGF agent is an anti-VEGF aptamer and is administered at a dosage of less than 0.3 mg to about 0.003 mg locally into the eye. In some embodiments, the anti-VEGF aptamer is administered at a dosage less than about 0.30 mg. Examples of such formulations are found in U.S. Patent Application Ser. No. 60/692,727; which is incorporated herein by reference in its entirety.

As used herein, "microparticles" refers to particles having a diameter of typically less than 1.0 mm, and more typically between 1.0 and 250 microns.

The microparticles of the present invention include, but are not limited to, microspheres, microcapsules, microsponges, microgranules and particles in general, with an internal structure comprising a matrix of agent and excipient. Microparticles may also include nanoparticles.

Microspheres are typically solid spherical microparticles. Microcapsules are typically spherical microparticles typically having a core of a different polymer, drug, or composition.

As used herein, the term "nanoparticles" refers to particles having a diameter of typically between about 20 nanometers (nm) and about 2.0 microns (μm), typically between about 100 nm and about 1.0 μm.

An "injection" is a preparation intended for parenteral administration. Injections include, but are not limited to, liquid preparations that are drug substances or solutions or suspensions thereof.

The grammatically correct and preferred term "intravitreous" is used herein and in the art. The term "intravitreal" is used colloquially as an alternative to the term "intravitreous" for injections into the eye's vitreous humor between the lens and the retina.

The term "controlled release" refers to control of the rate and/or quantity of biologically active molecules delivered according to the drug delivery formulations of the invention. The controlled release kinetics can be continuous, discontinuous, variable, linear or non-linear. This can be accomplished using one or more types of polymer compositions, drug loadings, inclusion of excipients or degradation enhancers, or other modifiers, administered alone, in combination or sequentially to produce the desired effect. "Controlled release" microparticles include, but are not limited to, "sustained release" microparticles and "delayed release" microparticles.

The term "sustained release" refers to releasing a biologically active agent into the body steadily, over an extended period of time. Sustained release formulations offer the ability to provide a subject with a biologically active agent over a time period greater than that achieved by a typical bolus administration of the biologically active agent. Sustained release microparticles may advantageously reduce the dosing frequency of a biologically active agent.

"Zero-order" or "linear release" is generally construed to mean that the amount of the biologically active molecule released over time remains relatively constant as a function of amount/unit time during the desired time frame. Multi-phasic is generally construed to mean that release occurs in more than one "burst".

The term "packed bed apparatus" refers to any vessel containing packing material capable of creating an emulsion upon contact with two immiscible fluids.

The term "biodegradable" or "bioerodible," as used herein, refer to polymers that dissolve or degrade within a period that is acceptable in the desired application (usually in vivo therapy), typically less than about five years, and more preferably less than about one year, once exposed to a physiological solution of pH ranging from about 6 to about 9 and at a temperature of ranging from about 25 C to about 38 C.

A variety of biodegradable polymers used for controlled release formulations are well known in the art. Suitable polymers for example include, but are not limited to, poly(hydroxy acids), poly(lactic acid), poly(glycolic acid), poly(lactic acid-co-glycolic acid), polycaprolactones, polyanhydrides, polycarbonates, polyamides, polyesters, polyorthoesters, polyhydroxybutryate, certain types of protein and polysaccharide polymers, and blends, copolymers or mixtures thereof.

The biodegradable polymers are optionally capped or uncapped. Capped polymers include, but are not limited to, those having esterified or amidated end groups. Un-capped polymers include free hydroxyl or carboxyl end-groups. In one embodiment, the microparticles comprise free-acid poly (lactic acid-co-glycolic acid). In another embodiment, the microparticles comprises lauryl or N-capped poly(lactic acid-co-glycolic acid).

Preferred polymers include poly (hydroxy acids). In one embodiment the polymer is poly (lactic acid-co-glycolic acid) ("PLGA") that degrade by hydrolysis following exposure to the aqueous environment of the body. The polymer is then hydrolyzed to yield lactic and glycolic acid monomers, which are normal byproducts of cellular metabolism. The rate of polymer disintegration can vary from several weeks to periods of greater than one year, depending on several factors including polymer molecular weight, ratio of lactide to glycolide monomers in the polymer chain, and stereoregularity of the monomer subunits (mixtures of L and D stereoisomers disrupt the polymer crystallinity enhancing polymer breakdown). Microparticles may contain blends of two and more biodegradable polymers, of different molecular weight and/or monomer ratio.

PLGA may have any suitable monomer ratio of lactide:glycolide. In one embodiment the amount of lactide ranges from 40-100%. In another embodiment the amount of glycolide ranges from 0-60%. In one embodiment, the PLGA has a monomer ratio of lactide:glycolide in the range of about 40:60 to 100:0. In another embodiment, the PLGA has a monomer ratio of lactide:glycolide in the range from about 45:55 to 100:0. In one particular embodiment, the PLGA has a monomer ratio of lactide:glycolide of about 50:50. In another particular embodiment, the PLGA has a monomer ratio of lactide:glycolide of about 65:35. In another particular embodiment, the PLGA has a monomer ratio of lactide:glycolide of about 75:25. The particular ratio of the polymers may be determined based on pharmacokinetic evaluations.

The microparticles may release a biologically active agent by any suitable means to allow for a controlled release of the biologically active agent. While not wishing to be bound by theory, the microparticles can release the biologically active agent by bulk erosion, diffusion or a combination of both.

A surfactant is optionally used in order to provide formulations that have the required syringability. In one embodiment, a surfactant is used for providing a stable emulsion during the process of forming the microparticles of the present invention. In another embodiment, a surfactant is used for preventing agglomeration during lyophilization during the process of forming the microparticles. In another embodiment, a surfactant is used for preventing agglomeration within the injection vehicle during the process of delivering the microparticles. Without wishing to be bound by theory, surfactants may provide batch-to-batch consistency of microparticles by forming a thin layer of material around the microparticles that helps prevent clumping. Any suitable surfactant may be used. Suitable surfactants include, but are not limited to, cationic, anionic, and nonionic compounds such as poly(vinyl alcohol), carboxymethyl cellulose, lecithin, gelatin, poly(vinyl pyrrolidone), polyoxyethylenesorbitan fatty acid ester (Tween 80, Tween 60, Tween 20), sodium dodecyl sulfate (SDS), mannitol and the like.

In one embodiment, the microparticles are formed using an emulsion comprising poly (vinyl alcohol). In a particular embodiment, the microparticles are formed using an emulsion comprising 1.0% poly (vinyl alcohol). The concentration of surfactant in the process medium is established to be an amount sufficient to stabilize the emulsion.

In one embodiment, the microparticles are lyophilized in a solution comprising SDS, Tween 20 or mannitol. In one particular embodiment, the microparticles are lyophilized in a solution comprising 7.8% SDS.

In one embodiment, the microparticles are suspended in an injection solution comprising SDS, Tween 20 or mannitol. In one particular embodiment, the microparticles are suspended in an injection solution comprising 0.5% SDS.

In one embodiment, the inherent viscosity of the biodegradable polymer may be in the range 0.1 to 2.0 dL/g. In another embodiment, the inherent viscosity of the biodegradable polymer ranges from about 0.1 to about 1.0 dL/g. In another embodiment, the inherent viscosity of the biodegradable polymer is about 0.16 dL/g, 0.35 dL/g or 0.61 dL/g.

Derivatized biodegradable polymers are also suitable for use in the present invention, including hydrophilic polymers attached to PLGA and the like. To form microparticles, in particular, a variety of techniques known in the art can be used. These include, for example, single or double emulsion steps followed by solvent removal. Solvent removal may be accomplished by extraction, evaporation or spray drying among other methods.

In a typical solvent extraction method, a polymer is dissolved in a continuous phase (e.g., an organic solvent) that is at least partially soluble in a discontinuous phase (e.g., an extraction solvent such as water). A biologically active molecule, either in soluble form or dispersed as fine particles, is then added to the polymer solution, and the mixture is dispersed into an aqueous phase that contains a surface-active agent such as poly (vinyl alcohol). The resulting emulsion is added to a larger volume of water where the organic solvent is removed by extraction or evaporation from the polymer/biologically active agent to form hardened microparticles.

Microparticles of the present invention may be prepared using any suitable method. In one embodiment, the microparticles are prepared using an emulsion process. A general scheme illustrating the process is shown in FIG. 8. In general, the methods combine a first phase and a second phase and pass the combination though an emulsifier. After an emulsion is formed, the solvent of the first phase is removed from the emulsion in an extractor, producing hardened microparticles. The microparticles are then sieved and dried.

In one embodiment, the methods have a first phase consisting of an organic solvent, a polymer and a biological or chemical agent dissolved or dispersed in the first solvent. The second phase comprises water and a stabilizer and, optionally, the first solvent. The first and the second phases are emulsified and, after an emulsion is formed, the first solvent is removed from the emulsion, producing hardened microparticles.

In another embodiment, the methods use a non-aqueous oil-in oil (o/o) process for making microparticles. In general an o/o method includes the steps of: a) dissolving a biocompatible polymer in a solvent to form a solution; b) combining a biologically active agent with the solution to produce a mixture; c) optionally combining the mixture of step (b) with a coacervating agent (optionally, while homogenizing the solution); and d) permitting the biocompatible polymer to form microparticles containing the biologically active agent. (See PCT Publication No. WO 03/092665 and K. G. Carrasquillo et al., "Controlled Delivery of the Anti-VEGF Aptamer EYE001 with Poly(lactic-co-glycolic) Acid Microspheres," *I.O.V.S.* (2003) 44(1), 290, each of which are hereby incorporated herein by reference in their entirety.)

In another embodiment, the methods use a water-in-oil-in-water (w/o/w) process for making microparticles. Such microparticles can be prepared by forming a primary water-in-oil emulsion comprising a water soluble molecule-containing solution as the inner aqueous phase and a polymer-containing solution as the oil phase. This primary emulsion can then be dispersed in an outer aqueous phase to form the final water-in-oil-in-water emulsion. The w/o/w tri-phasic emulsion can then be allowed to stir for a set period of time to promote extraction and evaporation of the organic solvent in which the solvent of the oil phase is removed and results in formation of hardened microparticles. Examples of w/o/w emulsion processes are described in U.S. Pat. Nos. 4,954,298; 5,330,767; 5,851,451 and 5,902,834, each of which are hereby incorporated herein by reference in their entirety. FIG. 5 illustrates an exemplary w/o/w process for forming microparticles of the present invention. Microparticles of the present invention, formed by a w/o/w process, are described in Example 2.

Emulsions may be formed by any suitable method. In one embodiment, a batch device for mixing the first and second phases under turbulent conditions such as with a stirrer as disclosed in U.S. Pat. No. 5,407,609, which is hereby incorporated herein by reference in its entirety. Other batch processes may employ a homogenizer or a sonicator. In another embodiment, an emulsion is formed by continuously mixing the first phase and second phase, in-line, using turbulent flow conditions, as in the use of an in-line dynamic mixer or an in-line static mixer such as described in U.S. Pat. No. 5,654,008, which is hereby incorporated herein by reference in its entirety.

In one embodiment, the microparticles are prepared according to the process disclosed in PCT publication No. WO 2005/003180, which is hereby incorporated by reference in its entirety, which discloses an emulsion-based technique employing a packed bed system that uses laminar flow conditions to produce an emulsion that results in microparticles containing biological or chemical agents after solvent removal.

The packed bed apparatus for the production of microparticles through an emulsion-based technique may be a vessel of any shape capable of being filled with packing material that allows liquid to flow through it (See FIG. 6). The apparatus of the present invention may further provide a material capable of insertion into both ends for enclosure of materials in such apparatus. FIG. 6 illustrates an exemplary apparatus according to one embodiment of the present invention. In this embodiment, a tube (1) is filled with beads as packing material (2).

Microparticle morphology is observed by Scanning Electron Microscopy (SEM) analysis. Microparticles are sputter coated with gold using an Anatech LTD Hummer 6.2 system. Scanning electron microscopic images were taken using a JEOL JSM-5600 scanning electron microscope and accompanying software at an accelerating voltage of 5-10 keV. For selected samples, SEM analysis of the internal microsphere structure was made after embedding microparticles in L.R. White Resin and then splitting the preparation after the resin hardened. Sample images are shown in FIGS. 1 and 2.

The microparticles of the present invention can be stored as a dry material such as a sterile lyophilized (or freeze dried) powder. In the instance of administration to a patient, prior to such use, the dry microparticles can be suspended in any pharmaceutically acceptable vehicle. Upon suspension, the microparticles may then be injected into the patient or otherwise utilized. Suitable pharmaceutically acceptable vehicles include, but are not limited to, a liquid vehicle, a suspension vehicle or an injection vehicle. The vehicle may include a surfactant, such as SDS, Tween 20 or mannitol.

Microparticles may be present in any suitable formulation. Methods well known in the art for making formulations are found, for example, in *Remington: The Science and Practice of Pharmacy* (20th ed., A. R. Gennaro ed., Lippincott: Philadelphia, 2000). Microparticles may be administered to humans, domestic pets, livestock, or other animals with a pharmaceutically acceptable diluent, carrier, or excipient. In one embodiment, the microparticles may be present in any suitable formulation for delivery to the eye.

Conventional pharmaceutical practice may be employed to provide suitable formulations or compositions to administer the identified compound to patients suffering from a disease, disorder, or condition of the eye. Administration may begin before, during, or after the patient is symptomatic.

In one embodiment, the microparticles are suspended in an acceptable pharmaceutical liquid vehicle, such as a 2.5 wt. % solution of carboxymethyl cellulose in water. In another embodiment, pegaptanib microparticles are suspended in an aqueous solution comprising 10 mM Sodium Phosphate, 136.9 mM Sodium Chloride, 2.7 mM Potassium Chloride, 0.05% Tween 20, and pH 7.4 (Filtered 0.2 μm). In another embodiment, pegaptanib microparticles are formulated for a dose of 1 mg of pegaptanib per 100 μL of microparticle solution. In another embodiment, pegaptanib microparticles are suspended in a solution comprising pegaptanib. In a particular embodiment, pegaptanib microparticles are suspended in a solution comprising pegaptanib formulated at 3.47 mg/mL, measured as the free acid form of the oligonucleotide, sodium chloride, monobasic sodium phosphate monohydrate, dibasic sodium phosphate heptahydrate, hydrochloric acid, and/or sodium hydroxide to adjust the pH and water for injection.

The volume of injection will depend on the route of administration. A typical intravitreous injection requires a 27 gauge needle or narrower and a delivered volume less than or equal to about 150 μL. A typical subconjunctival injection can accommodate a 23 gauge needle and a volume of up to 750 μL.

Sustained release formulations can be advantageous by reducing intravitreous (IVT) dosing frequencies of therapy involving biologically active agents. Applicants evaluated the in vivo release properties of pegaptanib-loaded microparticles as set forth in Example 9 and thereby demonstrated the feasibility of delivering pegaptanib over a period of approximately one month or more from a poly(lactide-co-glycolide) (PLGA) polymer based sustained release formulation.

Elimination of pegaptanib from the eye into systemic circulation is considered to be the rate-limiting step of pegaptanib's plasma pharmacokinetics. Therefore the plasma pharmacokinetics of pegaptanib should mirror the in vivo release of pegaptanib from the sustained release formulation. Following bilateral intravitreous (IVT) administration of liquid pegaptanib (pegaptanib sodium in phosphate buffered saline solution), plasma concentrations declined slowly overtime. The terminal phase rate constant, in plasma, reflected the slow absorption of pegaptanib from the eye into the systemic circulation after an IVT injection (see FIG. 12). Since it is expected that pegaptanib will be released in a sustained fashion from PLGA formulations into the vitreous, it is expected that the pegaptanib released into the vitreous will have distribution and clearance properties similar to those of pegaptanib administered by a phosphate buffered saline solution.

Figure 12:
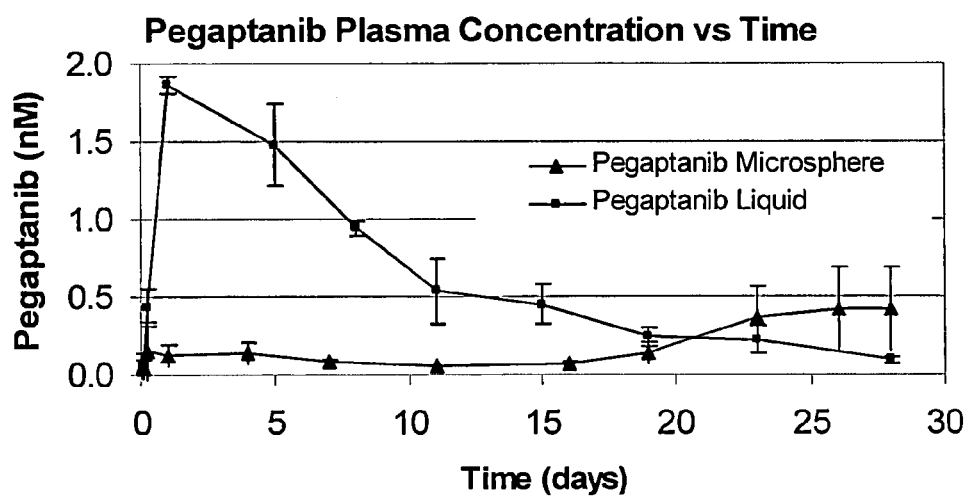
FIG. 12 is a graph depicting the results of 28 day in vivo release study. The graph shows pegaptanib concentration in rabbits plasma samples administered intravitreous with 5 mg of PLGA microparticles containing 15% weight percent pegaptanib.

Plasma concentrations resulting from a 28 day in vivo ocular distribution study in rabbits dosed intravitreously with 5 mg of PLGA microparticles containing 15% weight percent pegaptanib are shown in FIG. 12. The results show that the microparticles have a low burst release. A large burst release, common to PLGA formulations containing water soluble or hydrophilic compounds, is absent. In addition, plasma pegaptanib concentration levels were measured at a relatively constant level between 0.05-0.4 nM over the 28 day study period relative to an equivalent IVT liquid pegaptanib dose, indicating a sustained release of pegaptanib in the vitreous was achieved.

It is known in the art that modifying the polymer composition of a sustained release microparticle formulation affects the rate of polymer decomposition in vivo and therefore effects the release characteristics of the microparticle formulation. Therefore demonstrating a release duration of one month from a microparticle formulation in vivo indicates that a release duration of greater than one month from a microparticle formulation in vivo is feasible.

EXAMPLES

The following examples serve to illustrate certain useful embodiments and aspects of the present invention and are not to be construed as limiting the scope thereof. Alternative materials and methods can be utilized to obtain similar results.

Example 1

Preparation of Microparticles (Oil-in-Water)

Formulations were prepared via an oil-in-water solvent extraction/evaporation method. Macugen®; pegaptanib sodium ((OSI) Eyetech, Inc., NY, N.Y.) and PLGA were dissolved in methylene chloride and an emulsion was formed according to the process disclosed in PCT publication No. WO 2005/003180, which is incorporated herein by reference in its entirety. Following solvent extraction from the emulsion particles, the hardened microparticles were sieved through a 45 μm screen. Microparticles≤45 μm were collected by centrifugation and dried by lyophilization.

Example 2

Preparation of Pegaptanib Microparticles (Water-in-Oil-in-Water)

A batch size of 200 milligrams dry microspheres containing pegaptanib was prepared according to the following procedure:

Step 1. Preparation of Primary Aqueous Phase
  a. 30 mg Pegaptanib
  b. 300 µL water
  c. The mixture was vortexed to dissolve components Step 2. Preparation of Organic Phase
  a. 200 mg PLGA (i.e. 50:50 lactide:glycolide, IV=0.37 dL/g)
  b. 7 ml methylene chloride ($CH_2Cl_2$)
  c. The mixture was vortexed to dissolve components Step 3. Preparation of Secondary Aqueous Phase/Quench Solution
  b. 10.2 g polyvinyl alcohol
  c. 104 g sucrose
  d. 1.25 mL 1M Tris, pH 8.0
  e. 1 mL 0.5M EDTA, pH 8.0
  f. All components were dissolved in ~800 mL water. The pH was adjusted to 7.4 and the final volume to was brought to 1 L.

Step 4.
The organic solution was homogenized at 20000 RPM for a total of 2 minutes using a Virtis homogenizer. While homogenizing, the primary aqueous (drug containing) solution was slowly injected through 21G needle over 20 seconds to form primary water-oil emulsion.

Step 5.
The secondary aqueous phase (35 mL) was homogenized at 20000 RPM for 1 minute. The primary emulsion was immediately transferred into a beaker containing homogenized secondary aqueous phase to form a secondary water-oil-water emulsion.

Step 6.
The secondary emulsion was poured into a 250 mL beaker containing 100 mL quench solution (stirring speed=4) to extract $CH_2Cl_2$. Allowed to stir at room temperature for 3.5 hours.

Step 7.
The material was transferred to a collection vessel for centrifugation and washing.
  a. Centrifuged at 1500 RPM for 15 minutes and pour off supernatant.
  b. Repeated centrifugation and decanting of supernatant two more times.

Step 8.
The final pellet was re-suspended in DI water and lyophilize for about 96 hours (4 days). During first 24 hours on lyophilizer, the vacuum on system was purged every 2 hours.

Example 3

Morphology Analysis of Microparticles

Microparticle morphology was observed by Scanning Electron Microscopy (SEM) analysis. Microparticles were sputter coated with gold using an Anatech LTD Hummer 6.2 system. Scanning electron microscopic images were taken using a JEOL JSM-5600 scanning electron microscope and accompanying software at an accelerating voltage of 5-10 keV. For selected samples, SEM analysis of the internal microsphere structure was made after embedding microparticles in L.R. White Resin and then splitting the preparation after the resin hardened.

Scanning electron micrograph images of microparticles formed by the process as set forth in Example 1 are shown in FIGS. 1 and 2. The images of FIG. 1 show that the microparticles have a smooth external morphology. The image of FIG. 2 shows that the microparticles have a monolithic internal morphology.

Figure 3:
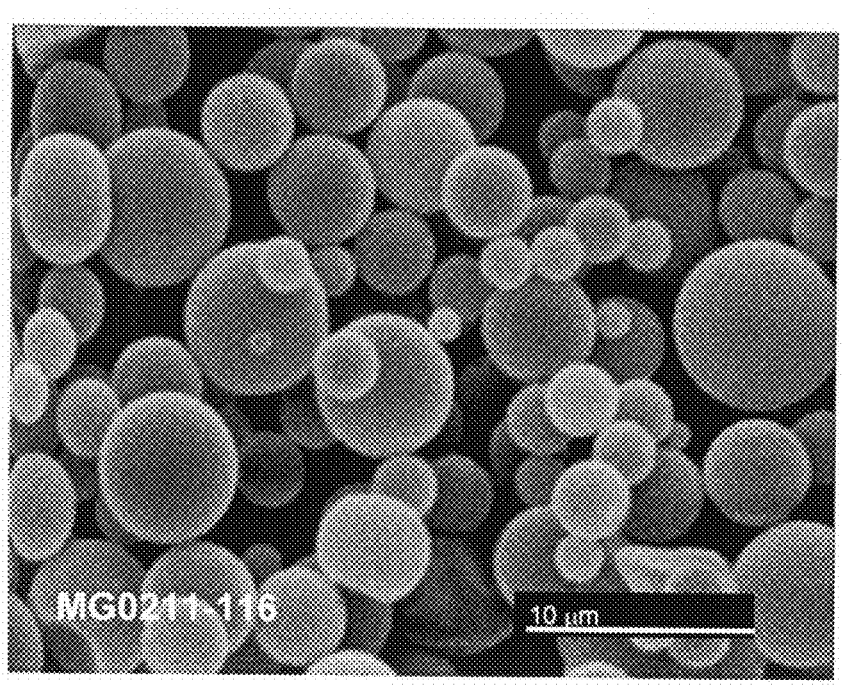
FIG. 3 is a scanning electron micrograph showing the external morphology of a sample of microspheres of the present invention formed by an water-in-oil-in-water process.
Figure 4:
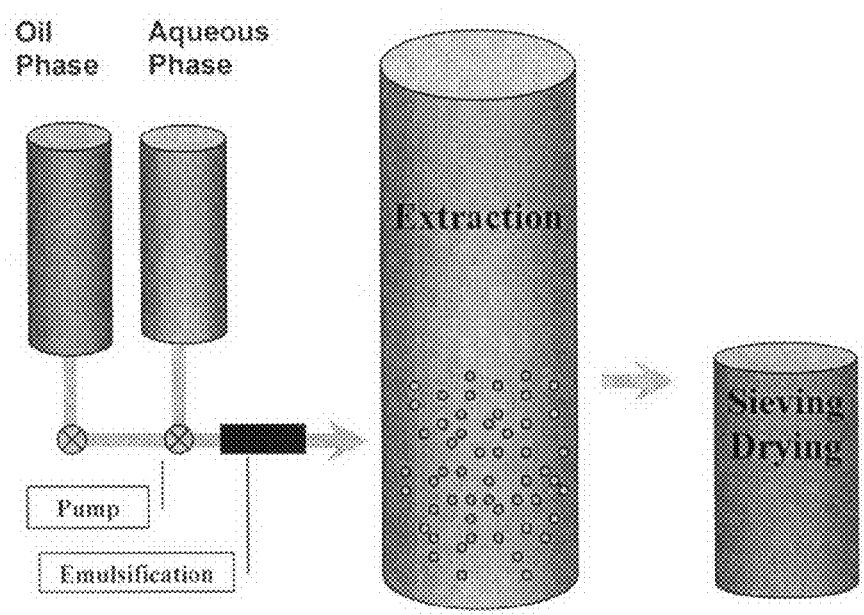
FIG. 4 is a schematic representation illustrating an exemplary oil-in-water process for forming microparticles of the present invention.
Figure 5:
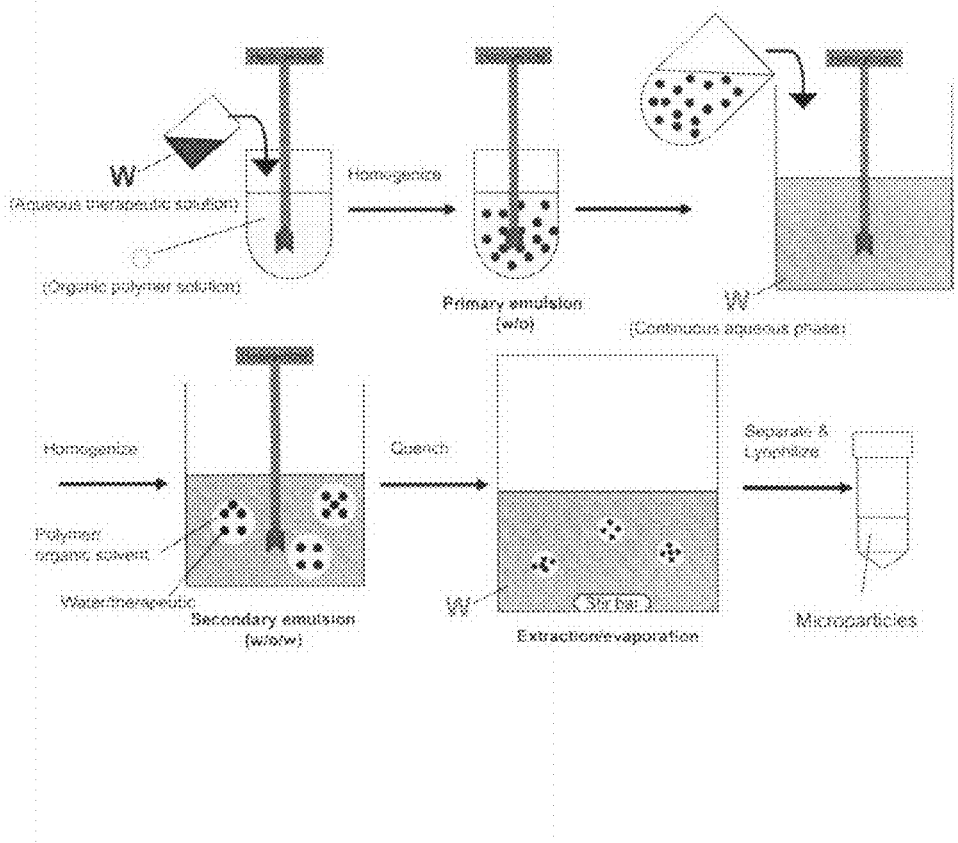
FIG. 5 is a schematic representation illustrating an exemplary water-in-oil-in-water process for forming microparticles of the present invention.
Figure 6:
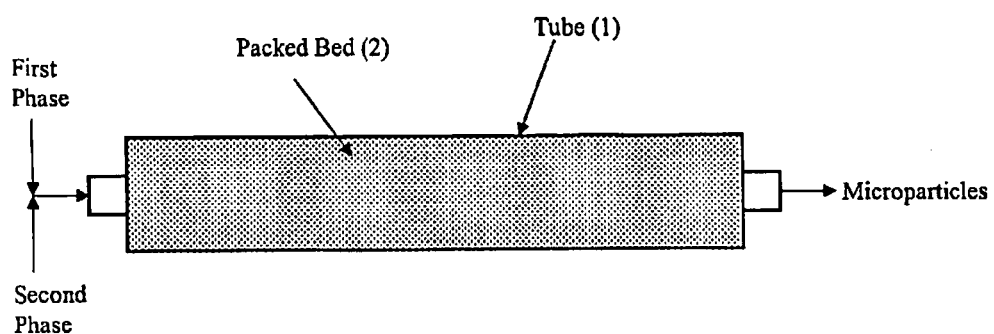
FIG. 6 is a schematic representation illustrating an exemplary packed bed apparatus with various components according to an embodiment of the present invention.
Figure 7:
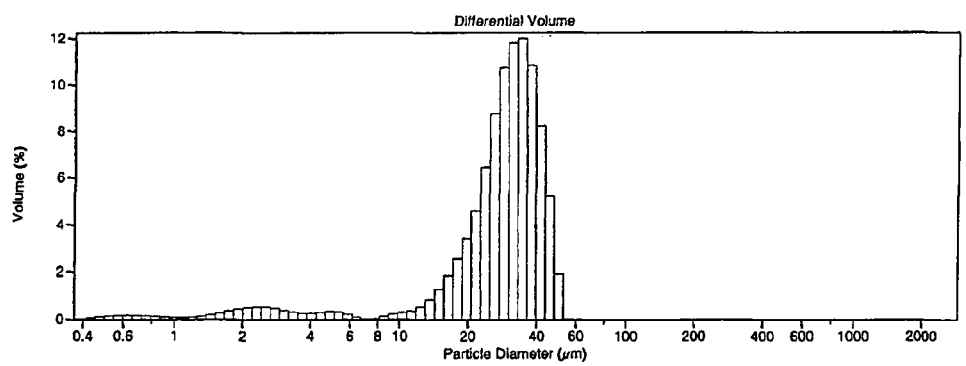
FIG. 7 is a chart representing particle size distribution of typical microparticles before sieving.

A scanning electron micrograph image of microparticles formed by the water-in-oil-in water process as set forth in Example 2 are shown in FIG. 3. The image shows that the microparticles have a particle size of less than about 10 µm and a smooth external morphology.

The in vitro and in vivo release analysis methods as set forth in Example 7 and Example 8 below indicate that the smooth, monolithic morphology of the microparticles release pegaptanib in a sustained release manner with a low burst.

Example 4

Analysis of Pegaptanib Coreload and Purity

Pegaptanib microspheres were prepared as set forth in Example 1 above. The microspheres were analyzed to determine if pegaptanib was degraded during their preparation. The microsphere preparations were characterized for Pegaptanib content and purity by HPLC. Approximately 6.5 mg of formulation was accurately weighed into a 2 mL microcentrifuge tube. The formulation was dissolved in 1.0 mL of 5% (water)/95% (acetonitrile), and the polymer precipitated by the addition of 1.0 mL 10-mM Na-phosphate pH 2.5. The resulting cloudy suspension was vortexed and clarified by centrifugation at 14,000 rpm for 2 minutes. Clear supernatant was assayed by HPLC. Samples were assayed against a 670.8 µg/mL EYE-001 (equivalent to 126.5 µg/mL oligomer) standard solution prepared in water and stored at −80° C.

Figure 8:
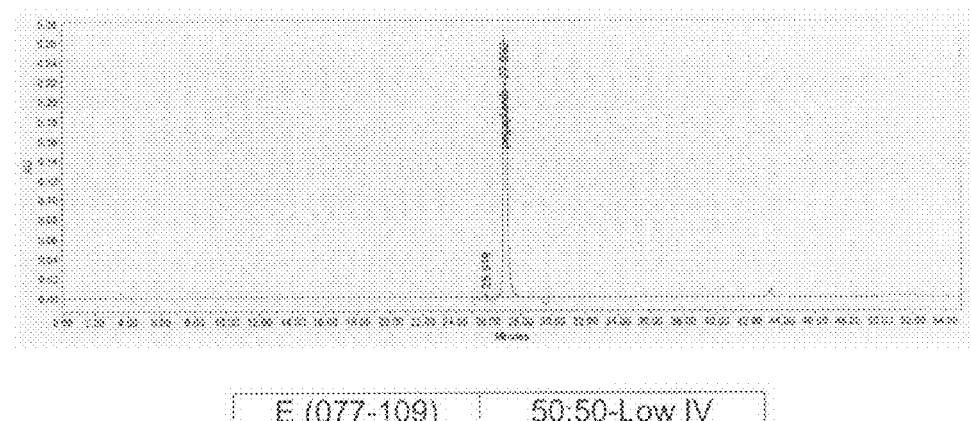
FIG. 8 shows a RP-HPLC chromatogram used to measure the core load and purity of pegaptanib extracted from microspheres.
Figure 9:
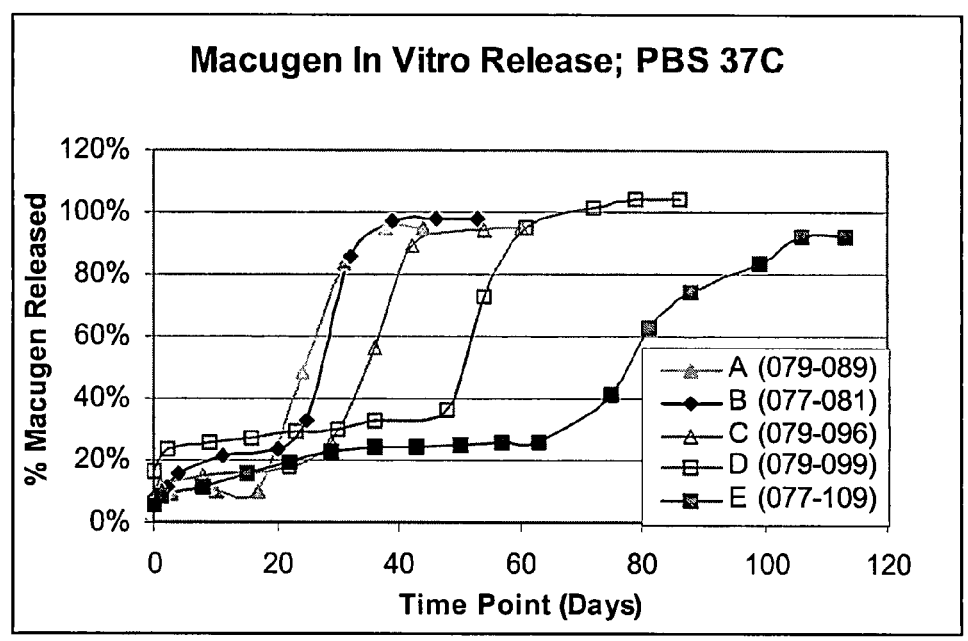
FIG. 9 is a graph depicting the release profiles of various pegaptanib-PLGA microparticles formed by an oil-in-water process. In vitro dissolution date demonstrating control release kinetics from Pegaptanib-PLGA microspheres.

FIG. 8 shows a RP-HPLC chromatogram used to measure the core load and purity of pegaptanib extracted from the microspheres. The chromatogram shows a high core load (12.3%) and that the purity of pegaptanib (99.18%) is unchanged by the formulation process.

Example 5

Analysis of Surfactant Effect on Lyophilization

Microparticles were prepared with 50:50-2.5 A (Alkermes) polymer and a 15% initial load of pegaptanib as set forth in Example 1. Following solvent extraction the microspheres were sieved through a 45 µm screen and collected on a 25 µm screen. The microspheres were washed with water and the batch was split in three. One fraction was lyophilized in water. The second fraction was lyophilized in SDS, such that the dried product was 7.8% (w/w) SDS. The third fraction was lyophilized in Tween20, such that the dried product was 0.24% (w/w) Tween20. In order to gauge suspendability and syringability, 100 µl vehicle was added to 20 mg pegaptanib microspheres in a 1.5 ml centrifuge tube. The following vehicles were tested: PBS; PBS with 0.5% SDS; PBS with 0.02% Tween20; PBS with 0.5% CMC; and PBS with 0.5% CMC and 0.2% Tween20. The mixture was suspended by tapping to determine ease of suspendability. The mixture was then vortexed for several seconds: The mixture was examined for uniformity of suspension and syringability. The results are shown in Table 1.

TABLE 1

|  | 077-141 | 077-141 0.24% Tween20 | 077-141 7.8% SDS | 077-151 2% Mannitol |
|---|---|---|---|---|
| PBS |  | Suspend easily Inject OK, slight clogging Little force required after settling | Suspend OK Some sticks to side Inject OK, slight clogging Little force required after settling | Visibly Clumpy Sticks to side Injects OK at first, worst with time |
| PBS + 0.02% Tween 20 | Difficult to suspend Inject Fine Settle quickly | Suspend easily Injects well Little force required after settling |  |  |
| PBS + 0.5% SDS |  |  | Suspend easily Injects well Little force required after settling Foamy |  |
| PBS + 0.5% CMC |  | Suspend OK Injects with some clogging | Suspend OK Inject OK Even after settling |  |
| PBS + 0.5% CMC + 0.02% Tween 20 | Very difficult to suspend Clog initially then OK | Suspend easily Injects well Stays in suspension well |  | Injects OK Even with settling |

Example 6

Analysis of Suspendability and Syringability

Aliquots of 10, 20 or 30 mg of pegaptanib microspheres, prepared by the method as set forth in Example 1, were added to 100 μL vehicle (0.5% CMC and 0.05% SDS in PBS). The mixture was examined for uniformity of suspension. The solution was then drawn into a 1 cc syringe through a ½ inch, 27 gauge needle and held for a time before pushing the sample out through the same needle. The procedure was repeated for a ½ inch, 29 gauge needle. The test was repeated after allowing microspheres to settle toward the syringe hub for 30 seconds. The following vehicles were tested: Saline; PBS; PBS with 0.05 or 0.5% SDS; PBS with 0.02% Tween20; PBS with 1% Mannitol; PBS with 0.5% SDS and 0.5% CMC; and PBS with 0.02% Tween20 and 0.5% CMC. The results are shown in Tables 2 and 3.

TABLE 2

|  | 100 mg microspheres/ml | 150 mg/ml | 200 mg microspheres/ml |
|---|---|---|---|
| Saline | Visibly clumpy Sticks to tube Injects fine |  |  |
| PBS | Sticks to tube Injects fine |  |  |
| PBS + 0.1% | Sticks to tube |  |  |
| SDS | Injects fine Force required after settling |  |  |
| PBS + 0.5% SDS | Injects fine Injects fine after settling Foamy |  | Difficult to suspend Settles quickly Clogs |
| PBS + 0.02% Tween$_{20}$ | Clogged initially, then injected fine Injects fine after settling | Difficult to suspend Clogs/pancakes | Difficult to suspend Withdraws nicely Pancakes on injection |
| PBS + 1% Mannitol | Sticks to tube Injects fine initially, then visible clumping |  |  |
| PBS + 0.5% CMC | Difficult to suspend Sticks to tube Injects fine Injects fine after settling |  |  |
| PBS + 0.5% CMC + 0.5% SDS | Difficult to suspend Injects fine Injects fine after settling |  |  |
| PBS + 0.5% CMC + 0.02% Tween$_{20}$ | Difficult to suspend Clogged on withdrawal Pancake formed on injection | Difficult to suspend Pancakes on injection |  |

TABLE 3

|  | >45 μm (Lot 077-132) | 45-38 μm (Lot 077-132) | | 38-25 μm (Lot 077-132) | | <25 μm (Lot 077-110) | |
|---|---|---|---|---|---|---|---|
|  | 100 mg/ml | 100 mg/ml | 200 mg/ml | 100 mg/ml | 200 mg/ml | 100 mg/ml | 200 mg/ml |
| PBS |  | clumps |  | clumps |  |  |  |
| PBS 0.05% SDS |  | clumps |  | clumps |  |  |  |
| PBS 0.5% | Can not draw into |  | Injects well | Injects well | Injects well | Injects well | Injects well |

TABLE 3-continued

| | >45 µm (Lot 077-132) | 45-38 µm (Lot 077-132) | | 38-25 µm (Lot 077-132) | | <25 µm (Lot 077-110) | |
|---|---|---|---|---|---|---|---|
| | 100 mg/ml | 100 mg/ml | 200 mg/ml | 100 mg/ml | 200 mg/ml | 100 mg/ml | 200 mg/ml |
| SDS | syringe | | Even w/ settling | Even w/ settling | Even w/ settling | | Even w/ settling |
| PBS, 0.02% Tween20 | | Injects well | | Injects well | | | |
| PBS 1% Mannitol | | | | clumps | | | |

Example 7

In Vitro Release of Pegaptanib Microspheres

The microspheres were analyzed to determine the in vitro release profile of pegaptanib. In vitro release of pegaptanib from microsphere formulations was determined in PBS (pH 7.4) containing 0.02% Tween-20 and 0.05% sodium azide. Typically 10 mg of microspheres were added to 1 mL buffer in a capped tube and placed in a shaking (150 cycles per minute) water bath incubator at 37° C. The release medium supernatant was sampled periodically and assayed for conjugate quantity and approximate purity by the reverse phase HPLC. The "burst release" was determined by the percentage of drug that was released in the first three hours of incubation.

The release profiles were characterized by a low initial burst release of pegaptanib in the first 24 hours of release followed by a period of sustained release ranging from 40 days to greater than 200 days dependent on the composition and inherent viscosity of the PLGA polymer used to prepare the formulation.

Example 8

In Vivo Release of Pegaptanib Microspheres

The in vivo duration of release for microsphere formulations produced according to Example 1 were assessed in New Zealand rabbits by monitoring blood plasma concentration after bilateral intravitreous dosing of the test formulations.

Microspheres containing pegaptanib were suspended in PBS injection vehicle containing 0.02% surfactant at a concentration of 100 mg microspheres per milliliter. A volume of 50 µL of the test formulation suspension was injected intravitreously into the eye using a 300 µL insulin syringe fitted with a 29G, half-inch needle to provide a 5 mg dose of test formulation Blood plasma samples were harvested at specified intervals and stored at −20° C. until analysis. Samples were analyzed for pegaptanib concentration via Dual Hybridization-PCR Assay.

Animals

Adult male New Zealand White rabbits, weighing approximately 2.5-4.0 kg were used.

Experimental Methodology

Animals were weighed and anesthetized with xylazine (5 to 10 mg/kg administered subcutaneously) followed by ketamine (35 to 50 mg/kg administered intramuscularly). One to two drops of Tropicamide® were administered to each eye prior to ophthalmic examination and dosing.

The intravitreal injections were administered on Study Day 1 by a board certified veterinary ophthalmologist (DACVO). For each of the intravitreal injections, the rabbit was placed in a lateral recumbent position and the eye was topically anesthetized with 1 to 2 drops of 0.1% proparacaine solution. The dose volume (for each eye) was 50 µL containing 5 mg of PLGA formulation. The test article was injected intravitreously using a 300 µL insulin syringe fitted with a 29G, half-inch needle, or other appropriately sized needle. The needle was inserted 1 to 2 mm posterior to the limbus in the superotemporal quadrant. The bevel was kept in an anterior position and the needle was advanced into the mid-vitreous. Antibiotic ointment (triple antibiotic or equivalent) was administered to the eye, following injection. The procedure was repeated on the opposite eye. The first day of dosing was designated as Study Day 1. Following dose administration on Study Day 1, the animals were observed for the duration of the study.

At the designated time point 2 mL of whole blood was collected from the lateral ear vein using potassium EDTA as the anti-coagulant. All samples were analyzed for pegaptanib concentrations via a dual hybridization-RT PCR Assay. The trapezoid rule method was used to calculate AUC and assess the relative bioavailability of pegaptanib release from PLGA microspheres. After the final blood collection, all animals were euthanized via anesthesia by ketamine:xylazine mixture followed by an overdose of sodium pentobarbital.

Statistical Analysis

Statistical analysis of dual hybridization-RT PCR data was performed using Graph Pad Prism® (GraphPad Software, Inc., San Diego, Calif.). Standard curve sample concentrations was calculated by a 4 parameter curve fit meeting appropriate statistical parameters.

Previous studies have demonstrated that after bilateral IVT administration of pegaptanib sodium in a phosphate buffered saline solution, pegaptanib vitreous and plasma concentrations decline in a well defined and predictable manner. The terminal phase rate constant was equivalent in both vitreous humor and plasma and reflects the slow absorption of pegaptanib from the eye into the systemic circulation after an IVT injection. Thus blood plasma levels were used as a marker for vitreous levels after intravitreous dosing of pegaptanib sodium in phosphate buffered saline.

It was expected that pegaptanib would be released in a sustained fashion from the test formulations into the vitreous and that the pegaptanib released into the vitreous would have distribution and clearance properties similar to the properties of pegaptanib dosed in a phosphate buffered saline solution. Thus, the plasma pharmacokinetics of pegaptanib reflected the in vivo release of pegaptanib from the sustained release formulation as elimination from the eye into systemic circulation. This was considered to be the rate-limiting step determining pegaptanib's plasma pharmacokinetics.

Example 9

Release Profiles of Pegaptanib Microspheres (Formulations 093-063, 093-003-1, and 093-059)

Pegaptanib microspheres having a core load between about 12 and 15 w/w % were prepared as set forth in Example 1. Formulations 093-063, 093-003-1, and 093-059 are summarized in Table 4. The formulations were sieved to provide microspheres having a particle size of less than 45 µm.

TABLE 4

| Lot No. | Drug Coreload (wt. %) | PLGA Polymer | 1-Day Burst (%) |
|---|---|---|---|
| 093-033-1 | 14.3 | 50:50 4A | 8.1 |
| 093-059 | 12.9 | 75:25 2A | 13.5 |
| 093-063 | 14.4 | 50:50 3A | 6.1 |

Figure 13:
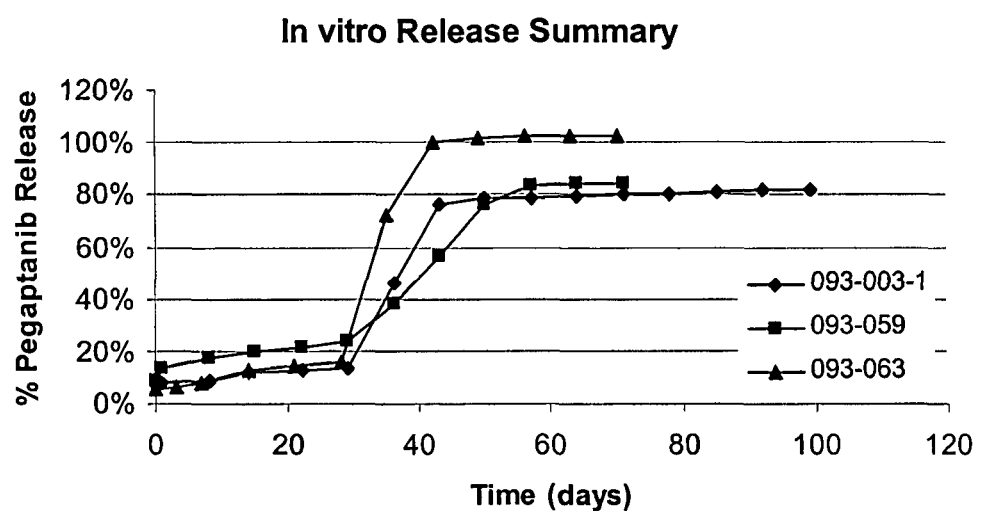
FIG. 13 is a graph depicting the in vitro release profile of PLGA pegaptanib microspheres suspended in PBS injection vehicle containing 0.02% surfactant at a concentration of 100 mg microspheres per milliliter over an 86 day study.

The in vitro release profile of the microspheres were analyzed as set forth in Example 7. The results of the in vitro release analysis are depicted in FIG. 13. The results shown in FIG. 13 demonstrate the sustained release properties of the microparticles of the present invention. The results also demonstrate that the microparticles of the present invention can be selectively designed to control the release of a biologically active agent over a desired time period. Preparing microspheres having various polymers demonstrated that the in vitro release of pegaptanib can be extended.

The in vivo release profile of the microspheres were analyzed as set forth in Example 8. The animal groups and blood collection schedule are summarized in Table 5.

Group Identification and Sampling Schedule

TABLE 5

| Group | Test Article | Pegaptanib Content (w/w %) | Route | Timepoints | Number of Eyes/ Timepoint | Number of Animals/ Timepoint | Total Number of Animals |
|---|---|---|---|---|---|---|---|
| Group 1M | Pegaptanib Microspheres 093-063 | 14.4% | Intravitreous | 2 and 6 hours post dose; and Study Days 2, 4, 9, 16, 23, 30, 37, 44, 51, 58, 65, 72, 79, and 86 | 12 | 6 | 6 |
| Group 2M | Pegaptanib Microspheres 093-003-1 | 14.3% | Intravitreous | 2 and 6 hours post dose; and Study Days 2, 4, 9, 16, 23, 30, 37, 44, 51, 58, 65, 72, 79, and 86 | 12 | 6 | 6 |
| Group 3M | Pegaptanib Microspheres 093-059 | 13.9% | Intravitreous | 2 and 6 hours post dose; and Study Days 2, 4, 9, 16, 23, 30, 37, 44, 51, 58, 65, 72, 79, and 86 | 12 | 6 | 6 |

Figure 14:
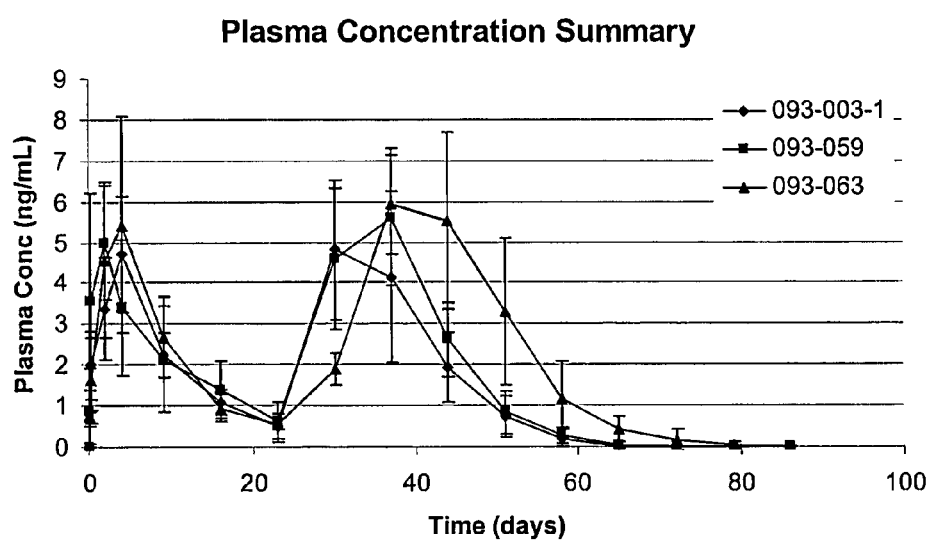
FIG. 14 is a graph depicting the results of 86 day in vivo release study in rabbits dosed intravitreously with 5 mg of PLGA microparticles containing 15% weight percent pegaptanib.
Figure 15:
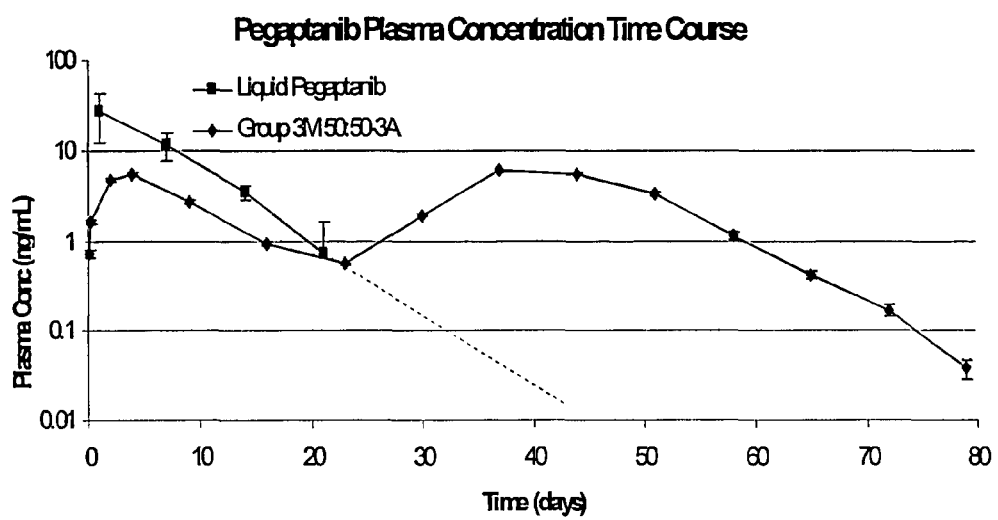
FIG. 15 is a graph depicting the results of 86 day in vivo release study in rabbits dosed intravitreously with 5 mg of PLGA microparticles containing 15% weight percent pegaptanib compared to liquid pegaptanib.

The in vivo release profile of the microspheres are illustrated in Table 6 and FIGS. 14 and 15. Pharmacokinetic data is presented in Table 7.

TABLE 6

| Formulation | 093-003-1 | | 093-059 | | 093-063 | |
|---|---|---|---|---|---|---|
| Polymer | 50:50-4A | | 75:25-2A | | 50:50-3A | |
| Drug Content | 14.2% | | 12.9% | | 14.4% | |
| API Dose (ug) | 134 | | 122 | | 136 | |
| Day | Ave (ng/mL) | Std Dev | Ave (ng/mL) | Std Dev | Ave (ng/mL) | Std Dev |
| 0.00 | 0.00 | 0.00 | 0.00 | 0.00 | 0.00 | 0.00 |
| 0.08 | 0.67 | 0.17 | 0.85 | 1.06 | 0.72 | 0.66 |
| 0.25 | 1.99 | 0.82 | 3.57 | 2.67 | 1.61 | 1.04 |
| 2 | 3.38 | 1.26 | 5.00 | 1.42 | 4.57 | 1.91 |
| 4 | 4.72 | 1.44 | 3.41 | 1.65 | 5.41 | 2.65 |
| 9 | 2.24 | 0.56 | 2.14 | 1.30 | 2.67 | 0.98 |
| 16 | 1.08 | 0.32 | 1.39 | 0.69 | 0.94 | 0.32 |
| 23 | 0.50 | 0.30 | 0.60 | 0.47 | 0.55 | 0.13 |

TABLE 6-continued

| Formulation | 093-003-1 | | 093-059 | | 093-063 | |
|---|---|---|---|---|---|---|
| Polymer | 50:50-4A | | 75:25-2A | | 50:50-3A | |
| Drug Content | 14.2% | | 12.9% | | 14.4% | |
| API Dose (ug) | 134 | | 122 | | 136 | |
| Day | Ave (ng/mL) | Std Dev | Ave (ng/mL) | Std Dev | Ave (ng/mL) | Std Dev |
| 30 | 4.81 | 1.71 | 4.60 | 1.73 | 1.90 | 0.38 |
| 37 | 4.15 | 2.09 | 5.61 | 1.69 | 5.94 | 1.22 |
| 44 | 1.93 | 0.85 | 2.62 | 0.90 | 5.52 | 2.16 |
| 51 | 0.74 | 0.50 | 0.84 | 0.53 | 3.29 | 1.80 |
| 58 | 0.20 | 0.21 | 0.28 | 0.19 | 1.14 | 0.95 |
| 65 | 0.00 | 0.00 | 0.03 | 0.08 | 0.42 | 0.31 |
| 72 | 0.00 | 0.00 | 0.00 | 0.00 | 0.17 | 0.24 |
| 79 | 0.00 | 0.00 | 0.00 | 0.00 | 0.04 | 0.09 |
| 86 | 0.00 | 0.00 | 0.00 | 0.00 | 0.00 | 0.00 |

FIGS. 14 and 15 show plasma concentrations resulting from an 86 day in vivo ocular study in rabbits dosed intravitreously with 5 mg of PLGA microparticles containing 15% weight percent pegaptanib are shown in FIGS. 14 and 15. FIG. 14 illustrates that three tested formulations all had low in vivo burst release followed by a period maintenance of blood plasma levels for 60-70 days. The in vitro release analysis of these formulations indicated similar release profiles for the three test formulations which was predictive of the in vivo performance.

FIG. 14 illustrates that the three tested formulations had in vivo release profiles that are well correlated with the in vitro release profiles for ranking burst and duration of release.

The plasma concentration curves demonstrate a controlled burst release that was well predicted by in vitro release analysis. In addition, a typical PLGA microsphere release profile is observed with a lag phase followed by polymer controlled secondary release phase resulting in a sustained plasma concentration above what is achieved by intravitreous dosing of the same dose of liquid pegaptanib sodium in rabbits. The bioanalytical analysis revealed that the blood plasma concentration of pegaptanib was sustained over a period of several weeks.

TABLE 7

| Formulation | Description | Dose (ug) | $AUC_{tot}$ ng*hr/mL | $F_{rel}$ | In vitro Burst | In vivo Burst |
|---|---|---|---|---|---|---|
| | Liquid | 141 | 4427 | 100% | | |
| 093-003-1 | 50:50-4A | 134 | 3173 | 75% | 8.08% | 7.20% |
| 093-059 | 75:25-2A | 122 | 3589 | 94% | 13.54% | 12.93% |
| 093-063 | 50:50-3A | 136 | 4429 | 104% | 6.06% | 5.83% |

Example 10

Release Profiles of Pegaptanib Microspheres (Formulations 093-023, 093-051, 077-189 and 093-041)

Pegaptanib microspheres having a core load between about 13 and 17 w/w % were prepared as set forth in Example 1. Formulations 093-023, 093-051, 077-189 and 093-041 are set forth in Table 8. The formulations were sieved to provide microspheres having a particle size of less than 45 μm.

TABLE 8

| Lot No. | Drug Coreload (wt. %) | PLGA Polymer | 1-Day Burst (%) |
|---|---|---|---|
| 093-023 | 13.6 | 50:50 5A | 32.8 |
| 093-051 | 14.1 | 65:35 3A | 3.4 |
| 077-189 | 16.1 | 75:25 4A | 5.2 |
| 093-041 | 13.6 | PLA 0.36 dL/g IV | 1.6 |

Figure 16:
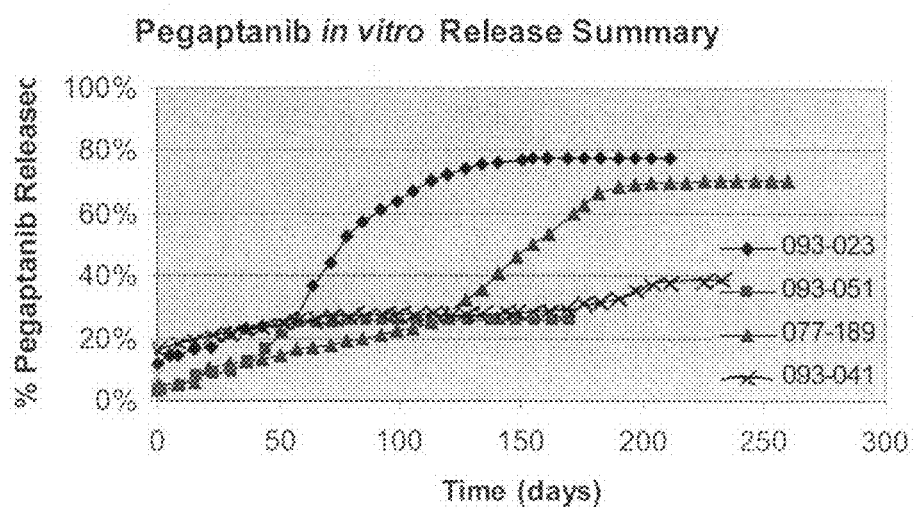
FIG. 16 is a graph depicting the in vitro release profile of PLGA pegaptanib microspheres suspended in PBS injection vehicle containing 0.02% surfactant at a concentration of 100 mg microspheres per milliliter over an 8 month study.

The in vitro release profile of the microspheres were analyzed as set forth in Example 7. The results of the in vitro release analysis of are depicted in FIG. 16. The results shown in FIG. 16 demonstrate the sustained release properties of the microparticles of the present invention. The results also demonstrate that the microparticles of the present invention can be selectively designed to control the release of a biologically active agent over a desired time period. Preparing microspheres having various polymers demonstrated that the in vitro release of pegaptanib can be extended.

The in vivo release profile of the microspheres were analyzed as set forth in Example 8. The in vivo release profile of the microspheres are illustrated in Table 9 and FIG. 17. Pharmacokinetic data is presented in Table 10.

TABLE 9

| Formulation | 093-023 | | 093-051 | | 077-189 | | 093.041 | |
|---|---|---|---|---|---|---|---|---|
| Polymer | 50:50-5A | | 65:35-3A | | 75:25-4A | | PLA (0.38) | |
| Drug Content | 13.6% | | 14.1% | | 16.1% | | 13.6% | |
| API Dose (ug) | 128 | | 133 | | 152 | | 128 | |
| Day | Ave (ng/mL) | Std Dev | Ave (ng/mL) | Std Dev | Ave (ng/mL) | Std Dev | Ave (ng/mL) | Std Dev |
| 0 | 0.00 | 0.00 | 0.00 | 0.00 | 0.00 | 0.00 | 0.00 | 0.00 |
| 0.08 | 0.79 | 0.40 | 0.15 | 0.30 | 0.69 | 0.97 | 0.25 | 0.33 |
| 0.25 | 2.59 | 1.13 | 0.60 | 0.26 | 1.78 | 1.12 | 1.45 | 0.96 |
| 1 | 5.83 | 3.67 | 1.91 | 0.25 | 2.81 | 0.96 | 3.78 | 2.41 |
| 3 | 3.23 | 1.84 | 1.20 | 0.32 | 2.38 | 1.09 | 2.73 | 1.38 |
| 7 | 2.55 | 0.61 | 1.02 | 0.28 | 2.47 | 1.36 | 1.86 | 0.73 |
| 14 | 1.64 | 0.65 | 1.45 | 0.39 | 1.23 | 0.31 | 1.21 | 0.10 |
| 21 | 0.99 | 0.35 | 0.73 | 0.22 | 0.72 | 0.31 | 0.60 | 0.17 |
| 28 | 3.43 | 0.92 | 0.46 | 0.11 | 0.46 | 0.04 | 0.22 | 0.18 |

TABLE 9-continued

| Formulation | 093-023 | | 093-051 | | 077-189 | | 093.041 | |
| --- | --- | --- | --- | --- | --- | --- | --- | --- |
| Polymer | 50:50-5A | | 65:35-3A | | 75:25-4A | | PLA (0.38) | |
| Drug Content | 13.6% | | 14.1% | | 16.1% | | 13.6% | |
| API Dose (ug) | 128 | | 133 | | 152 | | 128 | |
| Day | Ave (ng/mL) | Std Dev | Ave (ng/mL) | Std Dev | Ave (ng/mL) | Std Dev | Ave (ng/mL) | Std Dev |
| 35 | 7.28 | 2.10 | 3.24 | 2.22 | 0.25 | 0.05 | 0.00 | 0.00 |
| 42 | 3.06 | 0.94 | 6.96 | 2.45 | 0.25 | 0.07 | 0.00 | 0.00 |
| 49 | 1.50 | 0.52 | 5.63 | 1.38 | 0.38 | 0.09 | 0.00 | 0.00 |
| 56 | 0.60 | 0.17 | 2.63 | 1.03 | 1.25 | 0.50 | 0.00 | 0.00 |
| 63 | 0.11 | 0.12 | 0.56 | 0.18 | 2.75 | 0.82 | 0.00 | 0.00 |
| 70 | 0.03 | 0.06 | 0.26 | 0.14 | 3.64 | 1.33 | 0.00 | 0.00 |
| 77 | 0.00 | 0.00 | 0.00 | 0.00 | 3.16 | 1.54 | 0.00 | 0.00 |
| 84 | 0.00 | 0.00 | 0.00 | 0.00 | 1.53 | 0.83 | 0.00 | 0.00 |
| 91 | 0.00 | 0.00 | 0.00 | 0.00 | 0.78 | 0.35 | 0.00 | 0.00 |
| 98 | 0.00 | 0.00 | 0.00 | 0.00 | 0.35 | 0.16 | 0.00 | 0.00 |
| 105 | 0.00 | 0.00 | 0.00 | 0.00 | 0.14 | 0.22 | 0.00 | 0.00 |
| 112 | 0.00 | 0.00 | 0.00 | 0.00 | 0.00 | 0.00 | 0.00 | 0.00 |
| 119 | 0.00 | 0.00 | 0.00 | 0.00 | 0.00 | 0.00 | 0.00 | 0.00 |
| 126 | 0.00 | 0.00 | 0.00 | 0.00 | 0.00 | 0.00 | 0.00 | 0.00 |
| 133 | 0.00 | 0.00 | 0.00 | 0.00 | 0.00 | 0.00 | 0.00 | 0.00 |
| 140 | 0.00 | 0.00 | 0.00 | 0.00 | 0.00 | 0.00 | 0.00 | 0.00 |
| 147 | 0.00 | 0.00 | 0.00 | 0.00 | 0.00 | 0.00 | 0.00 | 0.00 |
| 154 | 0.00 | 0.00 | 0.00 | 0.00 | 0.00 | 0.00 | 0.00 | 0.00 |
| 161 | 0.00 | 0.00 | 0.00 | 0.00 | 0.00 | 0.00 | 0.03 | 0.08 |
| 168 | 0.00 | 0.00 | 0.00 | 0.00 | 0.00 | 0.00 | 0.05 | 0.13 |
| 175 | 0.00 | 0.00 | 0.00 | 0.00 | 0.00 | 0.00 | 0.18 | 0.28 |
| 182 | 0.00 | 0.00 | 0.00 | 0.00 | 0.00 | 0.00 | 0.47 | 0.53 |
| 196 | | | | | | | 1.44 | 0.34 |
| 210 | | | | | | | 1.71 | 0.72 |
| 217 | | | | | | | 1.25 | 0.48 |
| 224 | | | | | | | 0.93 | 0.47 |
| 231 | | | | | | | 0.62 | 0.24 |
| 238 | | | | | | | 0.31 | 0.15 |
| 245 | | | | | | | 0.18 | 0.16 |
| 252 | | | | | | | 0.12 | 0.15 |
| 259 | | | | | | | 0.00 | 0.00 |

Figure 17:
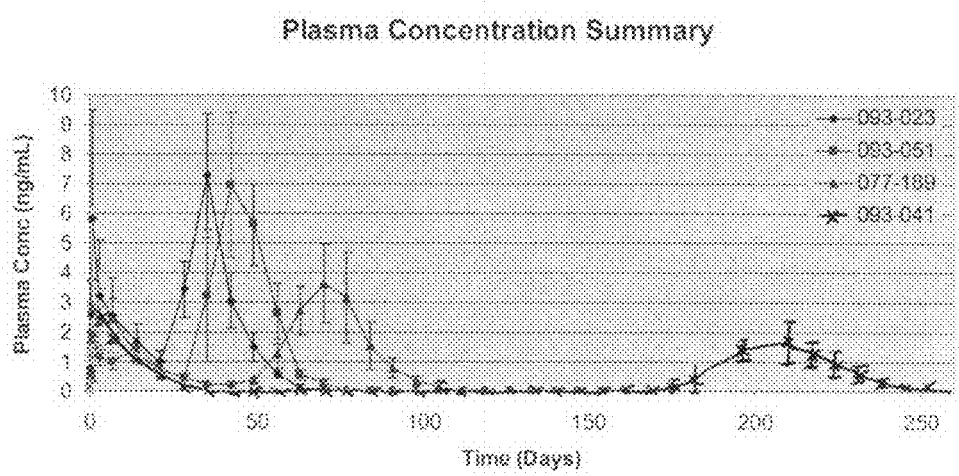
FIG. 17 is a graph depicting the results of 8 month in vivo release study in rabbits dosed intravitreously with 5 mg of PLGA microparticles containing 15% weight percent pegaptanib.

FIG. 17 depicts plasma concentrations resulting from an 8-month in vivo ocular study in rabbits dosed intravitreously with 5 mg of PLGA microparticles containing 15% weight percent pegaptanib. Of note is the absence of a large burst release common to PLGA formulations containing water soluble or hydrophilic compounds. Blood plasma levels were monitored as a surrogate marker for vitreous concentrations based on the established pharmacokinetics of Pegaptanib Sodium.

FIG. 17 illustrates that the four tested formulations all had low in vivo burst release followed by a period maintenance of blood plasma levels. The in vitro release analysis of these formulations indicated similar release profiles for the three test formulations which was predictive of the in vivo performance. FIG. 17 illustrates that the four tested formulations had in vivo release profiles that are well correlated with the in vitro release profiles for ranking burst and duration of release.

The plasma concentration curves demonstrate a controlled burst release that was well predicted by in vitro release analysis. The bioanalytical analysis revealed that the blood plasma concentration of pegaptanib was sustained over a period of several months.

TABLE 10

| Formulation | Description | Dose (ug) | $AUC_{tot}$ ng*hr/mL | $F_{rel}$ | In vitro Burst | In vivo Burst |
| --- | --- | --- | --- | --- | --- | --- |
| | Liquid | 141 | 4427 | 100% | | |
| 093-023 | 5050-5A | 128 | 3924 | 98% | 11.9% | 21.1% |
| 093-051 | 6535-3A | 133 | 3974 | 96% | 3.4% | 6.9% |
| 077-189 | 7525-4A | 151 | 3449 | 73% | 5.2% | 10.2% |
| 093-041 | PLA 0.36 | 128 | 2573 | 64% | 16.2% | 13.7% |

Example 11

In Vivo Release of Pegaptanib-Loaded Microparticles (Formulations 079-089 and 079-102)

Applicants evaluated the in vivo release properties of pegaptanib-loaded microparticles. Applicants administered pegaptanib-loaded poly(lactide-co-glycolide) (PLGA) microspheres, formed by the process as set forth in Example 1, intravitreously in New Zealand White rabbits and plasma samples were collected at various time points from 2 hours to 28 days as set forth in Table 11. This evaluation demonstrated the feasibility of delivering pegaptanib over a period of approximately one month or more from a (PLGA) polymer based sustained release formulation.

TABLE 11

| Group | Number of Time points | Number of animals/time point | Total Number of animals |
| --- | --- | --- | --- |
| Intravitreous Injection of Microspheres | 6 | 3 | 18 |
| Control Intravitreous Injection of Blank Microspheres | 2 | 3 | 6 |
| Control Intravitreous Injection of 50 µL 0.9% Sodium Chloride | 2 | 3 | 6 |
| Total Number of Animals | | | 30 |

Materials and Methods

PLGA microsphere formulations 079-089 and 079-102 were prepared as set forth in Example 1 above and were blended to provide sufficient material for animal dosing. Microspheres containing pegaptanib 15% on a weight percent basis were suspended in PBS injection vehicle containing 0.02% surfactant at a concentration of 100 mg microspheres per milliliter. The Pegaptanib-loaded PLGA microsphere formulations were administered by intravitreous injection (IVT) in New Zealand White rabbits. Placebo microspheres were dosed in an identical manner in control. Blood Plasma samples were collected at various time points, from 2 hours to 28 days as set forth in Table 10. Samples were stored at −20° C. until analysis. Samples were analyzed for pegaptanib concentration via a Dual Hybridization-PCR assay as set forth in Example 14. (see Patent Application Publication No. WO 2006/012468, which is incorporated herein by reference in its entirety).

Animals

Adult female New Zealand White rabbits, weighing approximately 2.5-4.0 kg were used. The groups are summarized in Table 11. The treatment schedule is summarized in Table 12.

Treatment Schedule

TABLE 12

| Group | Test Article | Route | Timepoints | Number of Eyes/ Timepoint | Number of Animals/ Timepoint | Total Number of Animals |
|---|---|---|---|---|---|---|
| Group 1 | Pegaptanib Microspheres | Intravitreous | 2 hour, 1, 5, 9, 14, 28 day | 6 | 3 | 18 |
| Group 2 | Blank Microspheres | Intravitreous | 1, 9 day | 6 | 3 | 6 |

Experimental Methodology

Intraocular pressure was measured in each animal prior to anesthesia using a hand-held applanation tonometer (Tonopen™). Animals were weighed and anesthetized with ketamine/xylazine administered intramuscularly. Tropicamide® were administered to each eye prior to ophthalmic examination. With the rabbit in right lateral recumbency, the left eye was topically anesthetized with 0.1% proparacaine solution.

A volume of 50 µL of the test article was injected intravitreously, using a 500 µL insulin syringe fitted with a 29G, half-inch needle, or other appropriately sized device. For Intravitreous injections, the needle was inserted 1-2 mm posterior to the limbus in the superotemporal quadrant. The bevel was kept in an anterior position and the needle was advanced into the mid-vitreous. Antibiotic ointment (triple antibiotic or equivalent) was administered to the eye following injection. The procedure was repeated on the right eye. Observations were recorded, including, but not limited to, leakage of test material from the injection site.

Whole blood (500 µL) was collected from the lateral ear vein. For animals in Group 1 (Day 28 time point), blood samples were collected at the following time points: 2 and 6 hours, 1, 3, 5, 9, 14, and 21 days, in addition to the terminal time point.

Statistical Analysis

Statistical analysis was performed using Graph Pad Prism. Samples are analyzed by 4 parameter curve fit meeting appropriate statistical parameters.

Results

Plasma concentrations resulting from a 28 day in vivo ocular distribution study in rabbits dosed intravitreously with 5 mg of PLGA microparticles containing 15% weight percent pegaptanib are shown in Table 13 and FIG. 12. The results show that the microparticles have a low burst release. A large burst release, common to PLGA formulations containing water soluble or hydrophilic compounds, is absent. In addition plasma pegaptanib concentration levels are measured at a relatively constant level between 0.05-0.4 nM over the 28 day study period relative to an equivalent IVT liquid pegaptanib dose, indicating a sustained release of pegaptanib in the vitreous was achieved.

It is known in the art that modifying the polymer composition of a sustained release microparticle formulation affects the rate of polymer decomposition in vivo and therefore effects the release characteristics of the microparticle formulation. Therefore demonstrating a release duration of one month from a microsphere formulation in vivo indicates that a release duration of greater than one month from a microsphere formulation in vivo is feasible.

TABLE 13

Pegaptanib Plasma Concentration Following Intravitreous Injection

| Pegaptanib Microsphere | | | Pegaptanib Liquid | | |
|---|---|---|---|---|---|
| Days | Conc (nM) | SD | Days | Conc (nM) | StDev |
| 0.08 | 0.055 | 0.078 | 0.08 | 0.051 | 0.05 |
| 0.25 | 0.142 | 0.200 | 0.25 | 0.436 | 0.12 |
| 1 | 0.126 | 0.065 | 1 | 1.861 | 0.06 |
| 4 | 0.137 | 0.067 | 5 | 1.476 | 0.26 |
| 7 | 0.080 | 0.014 | 8 | 0.941 | 0.04 |
| 11 | 0.051 | 0.005 | 11 | 0.539 | 0.21 |
| 16 | 0.069 | 0.016 | 15 | 0.451 | 0.13 |
| 19 | 0.138 | 0.070 | 19 | 0.241 | 0.06 |
| 23 | 0.362 | 0.203 | 23 | 0.219 | 0.09 |
| 26 | 0.423 | 0.273 | 28 | 0.088 | 0.02 |
| 28 | 0.415 | 0.271 | | | |

Example 12

Release Profile of Pegaptanib Microparticles (Water-in-Oil-in-Water)

Table 14 shows the properties of pegaptanib microparticles that were prepared as set forth in Example 2. The in vitro release profiles of the pegaptanib microparticles were determined by the process as set forth in Example 7

Figure 10:
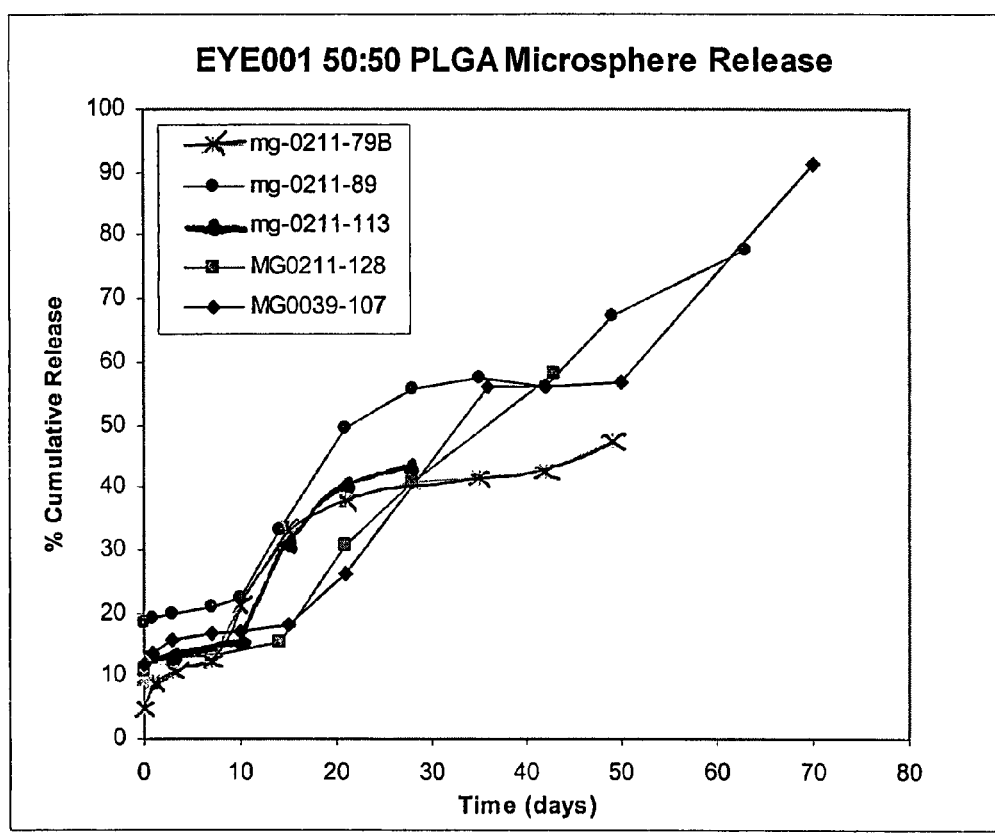
FIG. 10 is a graph depicting the release profiles of various pegaptanib-PLGA microparticles formed by an water-in-oil-in-water process. In vitro dissolution rate demonstrating control release kinetics from Pegaptanib-PLGA microspheres.

The release profiles of the microparticles from Table 14 are shown in FIG. 10. FIG. 10 is a graph depicting in vitro dissolution rate profiles demonstrating control release kinetics from Pegaptanib-PLGA microspheres.

TABLE 14

| Description | Yield | EYE001 Core Load (% w/w) | % Encapsulation Efficiency | Particle Size | Surface Morphology |
| --- | --- | --- | --- | --- | --- |
| EYE001 50:50 PLGA | 65.78% | 7.09 ± 0.84 | 46.14 ± 5.5 | <10 µm | Smooth |
| EYE001 50:50 PLGA | 66.02% | 7.05 ± 0.07 | 47.09 ± 0.45 | <10 µm | Smooth |
| EYE001 50:50 PLGA | 66.28% | 8.22 ± 0.09 | 52.8 ± 0.54 | NT | NT |
| Placebo 50:50 PLGA | 64.05% | n/a | n/a | <10 µm | Smooth |
| EYE001 50:50 PLGA | 56.49% | 9.02 ± 0.11 | 59.08 ± 0.69 | <10 µm | Smooth |
| Placebo 50:50 PLGA | 64.10% | n/a | n/a | <10 µm | Smooth |
| EYE001 50:50 PLGA | 87.01% | 7.70 ± 0.46 | 51.06 ± 3.04 | <10 µm | Smooth |

The results of the in vitro release analysis of are depicted in FIG. 10. FIG. 10 shows the release properties of microparticles formed by the w/o/w process as set forth in Example 2. The results shown in FIG. 10 demonstrate the sustained release properties of the microparticles of the present invention. The results also demonstrate that the microparticles of the present invention can be selectively designed to control the release of a biologically active agent over a desired time period. Preparing microspheres having various polymers demonstrated that the in vitro release of pegaptanib can be extended.

Example 13

Pegaptanib Inhibition of VEGF Induced Tissue Factor Expression in HUVEC Cells

Pegaptanib microspheres were prepared as set forth in Example 1 above. The microspheres were analyzed to determine if pegaptanib maintained its efficacy following release from the microspheres.

HUVEC cells were plated at $1.5 \times 10^5$ cells/well in complete medium (Cascade Biologics Medium 200, supplemented with Low Serum Growth Supplement and Penicillin, Streptomycin, and Amphotericin B (PSA)) in 24 well plates and allowed to attach overnight in a 37° C./5% $CO_2$ incubator. Sixteen hours later, complete media was removed and cells are washed once with 1% medium (Cascade Biologics Medium 200, supplemented with 1% Fetal Bovine Serum and PSA). Cells were then starved in the 1% medium for 4 hours in a 37° C./5% $CO_2$ incubator. During starvation, assay controls and samples were prepared. Assay controls included 1% medium alone (zero control), 1% medium with 12.5 ng/mL VEGF (VEGF induction control), and 1% medium with Pegaptanib at 10 nM (Pegaptanib control). The test microsphere samples were prepared at a concentration of 10 nM in 1% medium with VEGF (12.5 ng/mL). After 4 hours of starvation, media was removed and the prepared assay samples were added to respective wells. All controls and test samples were done in duplicate (2 wells each). Cells were treated for 1 hour in a 37° C./5% $CO_2$ incubator. After the 1 hour incubation, media was removed and cells were washed with sterile 1×PBS. Cells were then lysed with RLT/βME lysis buffer (Qiagen). Lysed cells were collected in sterile tubes and stored at −80° C. or used immediately for total RNA isolation. RNA isolation was performed using the Qiagen RNeasy® Protocol. cDNA was made and the Tissue Factor gene was quantitated using a typical Taqman® Real Time PCR protocol.

Figure 11:
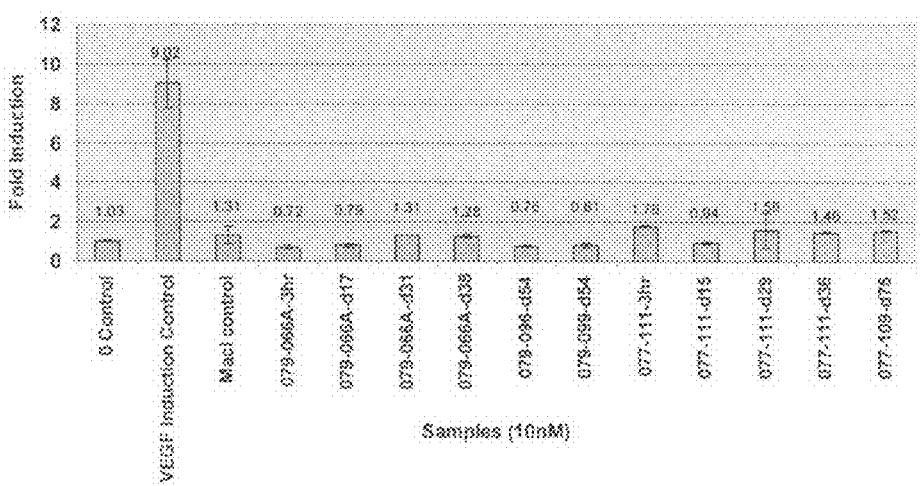
FIG. 11 is a graph depicting the results of cell proliferation assays of human umbilical vein endothelial cells (HUVEC) incubated with EYE001 formulations after release from PLGA microparticles.

The results of cell proliferation assays of human umbilical vein endothelial cells (HUVEC) incubated with EYE001 formulations after release from PLGA microparticles are shown in FIG. 11. The figure illustrates that addition of VEGF to the media increased expression of Tissue Factor by 9-fold. In the presence of 10 nM pegaptanib, Tissue Factor expression was reduced to basal levels. Pegaptanib released from PLGA microspheres had a similar effect on Tissue Factor expression as native pegaptanib. The results thereby demonstrated that the in vitro bioactivity of pegaptanib was unchanged by the microsphere fabrication process and subsequent in vitro release.

Example 14

Dual Hybridization-PCR Analysis of in Vivo Pegaptanib Release

Vitreous Digestion

Rabbit microsphere Vitreous samples are placed in 15 mL and 50 mL tubes and incubated overnight at 37° C. Following the incubation, Proteinase K (20 µL/sample) is added and the samples are incubated for 2 hours at 65° C. After 2 hours the samples are cooled to room temperature and then put in ice. The cooled samples are ready for dual hybridization assay. Plasma does not require digestion. 1×PBS and SDS is not added to the Vitreous digestion The digestion cocktail is prepared (per sample) as follows:

| | |
| --- | --- |
| 1×PBS | 500 µL |
| Hyaluronidase cocktail | 20 µL |
| Blendzyme III | 20 µL |
| SDS | 5 µL |
| DNAse | 10 µL |

Hyaluronidase cocktail is a mixture of 4 hyaluronidases in equal parts 5 µL. Each Hyaluronidase cocktail is a 1 mg/mL solution in 1×PBS and 1×BSA. Blendzyme (Roche Diagnostics Corporation Indianapolis, Ind.); Liberase Blendzymes are mixtures of highly purified collagenase and neutral protease enzymes, formulated for efficient, gentle, and reproducible dissociation of tissue from a wide variety of sources) is made as 7 mg/ml solution in 1×PBS. Proteinase K is made as 20 mg/ml solution in 1×PBS.

Dual Hybridization Assay
(Plasma)

Standards were prepared in 1× tissue (control tissue diluted 1:10). 165 µL of primer mix was added per sample into 0.2 PCR tubes. Primer mix was prepared by adding 1 µM detection primer to Hybridization buffer so that the final concentration of the detection primer in the required mixture was 1 nM. Standards or sample (25 µL) were added. Capture beads (5 µL) were added. The PCR tubes were then placed in a Thermal Cycler and programmed to run 75° C. for 15 minutes, 37° C. for 1 hour and then down to 25° C. Then the samples and standards were transferred from the PCR tubes into 96 well plates and 180 µL were transferred from each.

The plate was then run in a Kingfisher® 96 magnetic particle processor.

The following 96-well plates were prepared:
1-96 well plate (100 µL of water in each well)
5-96 well plates (200 µL of 1× wash buffer in each well)

The magnetic comb picked up the beads and moved them from plate to plate. The beads were washed in each plate leaving behind anything that was not specifically bound to the beads. The beads were deposited in the water plate at the end of the run. At this point the plate was ready to be run in Taqman® RT PCR.

Taqman® RT PCR

A 384-well plate was used. Total volume in a well was 10 µL. (Sample=4 µL; Cocktail=6 µL). A duplicate was prepared for each sample in the 96 well plate.

The following cocktail was prepared per 384 well:

| | |
|---|---|
| H20 | 0.4 µL |
| 2xPCR mix | 5 µL |
| Forward primer | 0.05 µL |
| Reverse primer | 0.05 µL |
| Probe | 0.5 µL |

First the cocktail was added and then the samples from the 96 well plate were transferred. The 384 well plate was spun in a centrifuge (1000 rpm) for less than a minute. The plate was then run in Taqman: 50° C. for 2 min, 95° C. for 10 min, and then 40 cycles of 95° C. 15 seconds to 60° C. for min.

Data Analysis

At the end of the run, data was available for the run from the SDS software. These data were then plugged in Microsoft Excel and Prism and the concentrations of the samples were then extrapolated from a standard curve.

The results of a 28 day in vivo release study of pegaptanib from PLGA microparticles are discussed in Example 11. FIG. 12 is a graph showing pegaptanib concentration in rabbits plasma samples dosed intravitreous or subconjunctival with 5 mg of PLGA microparticles containing 15% weight percent pegaptanib.

Example 15

Delayed Release Microparticle Pegaptanib Dosing Regimen

Step 1.
Administer a 100 µL pharmaceutical formulation comprising a bolus of about 0.3 mg free pegaptanib in solution and delayed release PLGA microparticles encapsulating about 35 mg pegaptanib.

Step 2.
The microspheres will have an initial burst of about 5-30% of pegaptanib and then will release at some rate constant over a predefined period.

Step 3.
At the end of the microsphere release profile, a second burst will occur releasing a second bolus of pegaptanib bringing the vitreal concentration to about 0.3 mg.

Step 4.
Four weeks post burst, during which time the polymeric metabolites are cleared, a new pegaptanib/microparticle injection would be administered as described in Step 1.

INCORPORATION BY REFERENCE

The patent and scientific literature referred to herein establishes knowledge that is available to those of skill in the art.

All patents, patent applications, and published references cited herein are hereby incorporated by reference in their entirety.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

We claim:

1. A sustained release suspension composition for intravitreal administration consisting essentially of a plurality of microparticles suspended in a pharmaceutically acceptable liquid carrier comprising phosphate buffer saline (PBS) and a surfactant comprising sodium dodecyl sulfate (SDS), wherein the liquid carrier is suitable for intravitreal administration, wherein
said microparticles comprise: (a) a biologically active anti-VEGF aptamer; and (b) poly(lactic acid) (PLA) or poly (lactic acid-co-glycolic acid) (PLGA) polymer and have a smooth, non-pitted external morphology, wherein said polymer has a monomer ratio of lactide:glycolide in the range of about 40:60 to 100:0;
said suspension comprises 100-300 mg microparticles per mL of said liquid carrier;
said microparticles release said biologically active anti-VEGF aptamer over a period of at least 40 days;
said microparticles have a particle size distribution in the range of 10 µm to 45 µm in diameter;
said microparticles comprise a PLA or PLGA polymeric material incorporating a core load of at least 7 wt % of said anti-VEGF aptamer and;
said microparticles release said anti-VEGF aptamer at an initial burst of less than 15 wt % of said core load within 24 hours of administration.

2. The composition of claim 1, wherein the microparticles release the anti-VEGF aptamer over a period of at least 3 months.

3. The composition of claim 1, wherein the microparticles release the anti-VEGF aptamer over a period of about 3-6 months.

4. The composition of claim 1, wherein the microparticles are syringable through a 29-gauge needle or narrower.

5. The composition of claim 1, wherein the microparticles have a mean diameter of about 30 µm.

6. The composition of claim 1, wherein the microparticles have a mean diameter of about 15 µm.

7. The composition of claim 1, wherein the microparticles are syringable through a 27-gauge needle or narrower and have a diameter of less than or equal to 75% of the inner diameter of the needle.

8. The composition of claim 1, wherein the microparticles are syringable through a 27-gauge needle or narrower and have a diameter of less than or equal to 50% of the inner diameter of the needle.

9. The composition of claim 1, wherein the microparticles are syringable through a 27-gauge needle or narrower and have a diameter of less than or equal to 25% of the inner diameter of the needle.

10. The composition of claim 1, wherein the microparticles have a core load of at least 10% by weight.

11. The composition of claim 1, wherein the microparticles have a core load of at least 15% by weight.

12. The composition of claim 1, wherein the microparticles have a core load of at least 20% by weight.

13. The composition of claim 1, wherein the microparticles exhibit a 24 hour burst of less than 10 wt % of said core load.

14. The composition of claim 1, wherein the microparticles exhibit a 24 hour burst of less than 5 wt % of said core load.

15. The composition of claim 1, wherein the microparticles form a homogeneous or un-agglomerated suspension with the pharmaceutically acceptable carrier.

16. The composition of claim 1, wherein the microparticles are microspheres.

17. The composition of claim 1, wherein the internal morphology of the microparticles is homogeneous or monolithic.

18. The composition of claim 1, wherein the anti-VEGF aptamer is a therapeutic agent suitable for the treatment of an ophthalmic disease or disorder.

19. The composition of claim 18, wherein the anti-VEGF agent is conjugated to a non-toxic, long-chain, hydrophilic, hydrophobic or amphiphilic polymer.

20. The composition of claim 19, wherein the anti-VEGF aptamer is conjugated to polyethylene glycol.

21. The composition of claim 20, wherein the anti-VEGF aptamer is pegaptanib.

22. The composition of claim 21 wherein pegaptanib is released from the microparticles at a rate ranging from about 0.01 to about 10 micrograms (μg) per day.

23. The composition of claim 22 wherein pegaptanib is present in an amount sufficient to provide pegaptanib plasma concentrations of about 0.05-0.40 nM throughout an administration period of at least 3 weeks.

24. The composition of claim 21 wherein the microparticles are suspended in a pegaptanib solution.

25. The composition of claim 1 wherein the liquid carrier further comprises a surfactant selected from the group consisting of poly(vinyl alcohol), carboxymethyl cellulose, lecithin, gelatin, poly(vinyl pyrrolidone), polyoxyethylenesorbitan fatty acid esters and mannitol.

26. The composition of claim 25 wherein the surfactant is selected from polyoxyethylenesorbitan fatty acid esters and mannitol.

27. A sustained release suspension composition consisting essentially of a plurality of microparticles having a smooth, non-pitted external morphology suspended in a pharmaceutically acceptable liquid carrier comprising phosphate buffer saline (PBS) and a surfactant comprising sodium dodecyl sulfate (SDS), wherein the liquid carrier is suitable for intravitreal administration, wherein said microparticles form a homogeneous or un-agglomerated suspension with the pharmaceutically acceptable carrier, said suspension comprises 100-300 mg microparticles per mL of said liquid carrier; wherein said microparticles comprise a poly(lactic acid-co-glycolic acid) (PLGA) polymeric material having a monomer ratio of lactide:glycolide of 75:25 and incorporating a core load of at least 7 wt % of pegaptanib, wherein said microparticles have a particle size distribution in the range of 10 μm to 45 μm in diameter, wherein said microparticles release pegaptanib over a period of at least 40 days at an initial burst of less than 15 wt % of said core load within 24 hours of administration, wherein pegaptanib is released from the microparticles at a rate ranging from about 0.01 to about 10 micrograms (μg) per day, and wherein said microparticles are syringable through a 27-gauge needle or narrower.

28. The composition of claim 27 wherein pegaptanib is released from the microparticles at a rate ranging from about 0.1 to about 6 μg per day.

29. The composition of claim 27 wherein pegaptanib is released at a rate sufficient to achieve pegaptanib plasma concentrations of about 0.05-0.40 nM throughout an administration period of at least 3 weeks.

30. The composition of claim 27 wherein pegaptanib is released at a rate sufficient to achieve pegaptanib plasma concentrations of about 0.05-0.40 nM throughout an administration period of at least 6 weeks.

31. The composition of claim 27, wherein the microparticles release pegaptanib over a period of at least 3 months.

32. The composition of claim 27, wherein the microparticles have a core load of at least 10% by weight.

33. The composition of claim 27, wherein the microparticles exhibit a 24 hour burst of less than 10 wt % of said core load.

34. The composition of claim 27, wherein the microparticles exhibit a 24 hour in vitro burst of less than 5 wt % of said core load.

35. The composition of claim 27, wherein the carrier further comprises a pharmaceutically acceptable surfactant or excipient.

36. The composition of claim 1, wherein the microparticles release the anti-VEGF aptamer over a period of at least 180 days.

37. The composition of claim 1, wherein the microparticles release the anti-VEGF aptamer over a period of at least 365 days.

38. The composition of claim 27, wherein the microparticles release the anti-VEGF aptamer over a period of at least 180 days.

39. The composition of claim 27, wherein the microparticles release the anti-VEGF aptamer over a period of at least 365 days.

* * * * *